US012656353B2

(12) United States Patent
Plavina et al.

(10) Patent No.: US 12,656,353 B2
(45) Date of Patent: Jun. 16, 2026

(54) BIOMARKERS OF PROGRESSIVE MULTIFOCAL LEUKOENCEPHALOPATHY

(71) Applicant: Biogen MA Inc., Cambridge, MA (US)

(72) Inventors: Tatiana Plavina, North Reading, MA (US); Carol Margaret Singh, Somerville, MA (US)

(73) Assignee: Biogen MA Inc., Cambridge, MA (US)

( * ) Notice: Subject to any disclaimer, the term of this patent is extended or adjusted under 35 U.S.C. 154(b) by 1211 days.

(21) Appl. No.: 17/429,767

(22) PCT Filed: Feb. 11, 2020

(86) PCT No.: PCT/US2020/017600
§ 371 (c)(1),
(2) Date: Aug. 10, 2021

(87) PCT Pub. No.: WO2020/167715
PCT Pub. Date: Aug. 20, 2020

(65) Prior Publication Data
US 2022/0128578 A1    Apr. 28, 2022

Related U.S. Application Data

(60) Provisional application No. 62/804,701, filed on Feb. 12, 2019.

(51) Int. Cl.
*G01N 33/68*    (2006.01)

(52) U.S. Cl.
CPC ..... *G01N 33/6896* (2013.01); *G01N 2800/50* (2013.01)

(58) Field of Classification Search
CPC ....................... G01N 33/6896; G01N 2800/50
USPC ......................................................... 435/7.1
See application file for complete search history.

(56) References Cited

U.S. PATENT DOCUMENTS

| | | |
|---|---|---|
| 8,465,727 B2 | 6/2013 | Bowser |
| 9,415,119 B2 | 8/2016 | Passini et al. |
| 10,369,193 B2 | 8/2019 | Passini et al. |
| 10,385,341 B2 | 8/2019 | Swayze |
| 10,669,546 B2 | 6/2020 | Swayze |
| 10,968,453 B2 | 4/2021 | Swayze |
| 11,474,113 B2 | 10/2022 | Farwell |
| 2005/0019915 A1 | 1/2005 | Bennett et al. |
| 2009/0042900 A1 | 2/2009 | Singh et al. |
| 2010/0267073 A1 | 10/2010 | Przedborski et al. |
| 2015/0285822 A1 | 10/2015 | Zhang et al. |
| 2016/0051699 A1 | 2/2016 | Passini et al. |
| 2017/0037410 A1 | 2/2017 | Swayze |
| 2017/0087212 A1 | 3/2017 | Passini et al. |
| 2017/0239225 A1 | 8/2017 | Androphy et al. |
| 2017/0363643 A1 | 12/2017 | Rigo et al. |
| 2019/0298708 A1 | 10/2019 | Jain |
| 2020/0040342 A1 | 2/2020 | Swayze |
| 2020/0239912 A1 | 7/2020 | Sah |
| 2020/0354723 A1 | 11/2020 | Swayze |
| 2021/0041459 A1 | 2/2021 | Farwell |
| 2021/0172963 A1 | 6/2021 | Benatar |
| 2022/0034907 A1 | 2/2022 | Ferguson |
| 2023/0107651 A1 | 4/2023 | Farwell et al. |

FOREIGN PATENT DOCUMENTS

| | | |
|---|---|---|
| CN | 102459611 | 5/2012 |
| CN | 104853778 | 8/2015 |
| CN | 106459972 | 2/2017 |
| CN | 107083400 | 8/2017 |
| CN | 107109407 | 8/2017 |
| JP | 2009545617 | 12/2009 |
| KR | 20120006073 | 1/2012 |
| RU | 2655811 | 5/2018 |
| WO | WO2007002390 | 1/2007 |
| WO | WO2010129021 | 11/2010 |
| WO | WO2014110291 | 7/2014 |
| WO | WO2015153800 | 10/2015 |
| WO | WO2015161170 | 10/2015 |
| WO | WO2016040748 | 3/2016 |
| WO | WO2017207600 | 12/2017 |
| WO | WO2018218219 | 11/2018 |
| WO | WO2019147960 | 8/2019 |
| WO | WO2020061355 | 3/2020 |
| WO | WO2020117772 | 6/2020 |
| WO | WO2020123783 | 6/2020 |
| WO | WO2020167715 | 8/2020 |
| WO | WO2010148249 | 12/2020 |

OTHER PUBLICATIONS

Dalla Costa et al., Serum neurofilament light chain levels are increased at the onset of PML in natalizumab treated MS patients (Pt.383), Neurology, Apr. 10, 2018; 90 (15 Supplement), first published on Apr. 9, 2018. (Year: 2018).*
Dalla Costa et al., Serum NeurofilamentLight Chain Levels are Increased at the Onset of PML in Natalizumab Treated MS Patients, Multiple Sclerosis Journal, October of 2017, vol. 23, pp. 368-369, 1 Olivers yard, 55 city road, London ec1y 1sp, England: Sage publications LTD. (Year: 2017).*
Wattjes et al., Diagnosis of natalizumab-associated progressive multifocal leukoencephalopathy using MRI, Curr Opin Neurol 2014, 27: 260-270. (Year: 2014).*
McGuigan et al., Stratification and monitoring of natalizumab associated progressive multifocal leukoencephalopathy risk: recommendations from an expert group, J Neurol Neurosurg Psychiatry, 2016, 87:117-125. (Year: 2016).*
Marcovitch, H. (Ed.). (2018). Biomarker, In Black's Medical Dictionary, 43rd Edition (43rd ed.), A& C Black. https://search.credoreference.com/articles/Qm9va0FydGljbGU6NTg5MTA5?aid=279753. (Year: 2018).*

(Continued)

*Primary Examiner* — Gregory S Emch
*Assistant Examiner* — Omar Ramadan
(74) *Attorney, Agent, or Firm* — Fish & Richardson P.C.

(57) ABSTRACT

Featured are biomarkers for progressive multifocal leukoencephalopathy (PML). Also provided are methods for reducing the occurrence or severity of PML during immunomodulator therapy or identification of PML in an immunocompromised subject.

9 Claims, 3 Drawing Sheets

Specification includes a Sequence Listing.

(56) References Cited

OTHER PUBLICATIONS

Amor et al., "Neurofilament Light Antibodies in Serum Reflect Response to Natalizumab Treatment in Multiple Sclerosis", Multiple Sclerosis Journal, Sep. 2014, 20(10:1355-1362.

Bacioglu et al., "Neurofilament Light Chain in Blood as CSF as Marker of Disease Progression in Mouse Models and in Neurodegenerative Diseases", Neuron, Jul. 2016, 91(1):56-66.

Benatar et al., "Neurofilament Light: A Candidate Biomarker of Presymptomatic Amyotrophic Lateral Sclerosis and Phenoconversion: Neurofilament Light in Presymptomatic ALS", Annals of Neurology, Jul. 2018, 84(1):130-139.

Boido et al., "Neuromuscular Junctions as Key Contributors and Therapeutic Targets in Spinal Muscular Atrophy," Front Neuroanat, Feb. 3, 2016, 10(6):1-10.

Byme et al., "Neurofilament light protein in blood as a potential biomarker of neurodegeneration in Huntington's disease: a retrospective cohort analysis," Lancet Neuro., Aug. 2017, 16: 601-609.

Calabresi et al., "Serum Neurofilament Light (NFL): Towards a Blood Test for Prognosis and Disease/Treatment Monitoring in Multiple Sclerosis Patients", Neurology, Apr. 2018, 90(15): Supp. 1.

Chiriboga et al., "Nusinersen for the Treatment of Spinal Muscular Atrophy," Expert Rev Neurother, Sep. 8, 2017, 17(10):955-962.

Cifuentes-Diaz et al., "Neurofilament Accumulation at the Motor Endplate and Lack of Axonal Sprouting in a Spinal Muscular Atrophy Mouse Model", Human Molecular Genetics, Jun. 2002, 11(12): 1439-1447.

Disanto et al., "Serum Neurofilament Light: A Biomarker of Neuronal Damage in Multiple Sclerosis: Serum NFL as a Biomarker in MS", Annals of Neurology, Jun. 2017, 81(6):857-870.

Gunnarson et al., "Axonal Damage in Relapsing Multiple Sclerosis is Markedly Reduced by Natalizumab", Annals of Neurology, Jan. 2011, 69(1):83-89.

International Preliminary Report on Patentability in International Appln. No. PCT/US2019/015185, dated Aug. 6, 2020, 8 pages.

International Preliminary Report on Patentability in International Appln. No. PCT/US2019/051992, dated Apr. 1, 2021, 12 pages.

International Search Report and Written Opinion in International Appln. No. PCT/US2019/015185, dated Apr. 10, 2019, 16 pages.

International Search Report and Written Opinion in International Appln. No. PCT/US2019/051992, dated Jun. 24, 2020, 21 pages.

International Search Report and Written Opinion in International Appln. No. PCT/US2019/064190, dated Mar. 4, 2020, 16 pages.

Khalil et al., "Neurofilaments as biomarkers in neurological disorders," Nature Reviews Neurology, Oct. 2018, 14:577-589.

Kiernan, "Progress towards therapy in motor neuron disease," Nature Reviews Neurology, Jan. 2018, 2 pages.

Kuhle et al., "Neurofilament Light and Heavy Subunits Compared as Therapeutic Biomarkers in Multiple Sclerosis," ACTA Neurologica Scandinavica, Dec. 2013, 128(6):E33-E36.

Linker et al., "Innovative Monoclonal Antibody Therapies in Multiple Sclerosis", Therapeutic Advances in Neurological Disorders, Jul. 2008, 1(1):33-42.

Lu et al., "Neurofilament Light Chain: A Prognostic Biomarker in Amyotrophic Lateral Sclerosis", American Academy of Neurology, 2015, 84:2247-2257.

Lu et al., "Plasma Neurofilament Heavy Chain Levels Correlate to Markers of Late State Disease Progression and Treatment Response in SOD1G93A Mice that Model ALS", PLoS One, Jul. 2012, 7(7):e40998.

McCampbell et al.., " Antisense Oligonucleotides Extend Survival and Reverse Decrement in Muscle Response in ALS Models", The Journal of Clinical Investigation, 2018, 128(8):3558-3567.

Novakova et al., "Monitoring Disease Activity in Multiple Sclerosis using Serum Neurofilament Light Protein", Neurology, Nov. 2017, 89(22):2230-2237.

Novakova et al., "Reduced Cerebrospinal Fluid Concentrations of Oxysterols in Response to Natalizumab Treatment of Relapsing Remitting Multiple Sclerosis", Journal of Neurological Sciences, Aug. 2015, 358(1):201-206.

Puentes et al., "Immune Reactivity to Neurofilament Proteins in the Clinical Staging of Amytrophic Lateral Sclerosis", Journal Neurol. Neurosurg. Psychiatry, Sep. 2013, pp. 1-5.

Rosengren et al., "Patients with Amyotrophic Lateral Sclerosis and Other Neurodegenerative Diseases have Increased Levels of Neurofilament Protein in CSF", Journal of Neurochemistry, Nov. 1996, 67(5): 2013-2018.

Rossi et al., "CSF Neurofilament Proteins as Diagnostic and Prognostic Biomarkers for Amyotrophic Lateral Sclerosis", Journal of Neurology—Zeitschrift Fuer Neurologie, Jan. 2018, 265(3):510-521.

Spinraza (nusinersen) injection, for intrathecal use, FDA, Label Dec. 2016, 13 pages.

Totzeck et al., "Neurofilament Heavy Chain and Tau Protein Are Not Elevated in Cerebrospinal Fluid of Adult Patients with Spinal Muscular Atrophy during Loading with Nusinersen," Int. J. Mol. Sci., Oct. 2019, 20(5397):1-10.

Weston et al., "Serum neurofilament light in familial Alzheimer disease," Neurology, Nov. 2017, 89:2167-2175.

Wurster et al., "Neurochemical Markers in CSF of Adolescent and Adult SMA Patients Undergoing Nusinersen Treatment", Therapeutic Advances in Neurological Disorders, May 2019, pp. 1-8.

Wurster et al., "Neurofilament Light Chain in Serum of Adolescent and Adult SMA Patients Under Treatment with Nusinersen", Journal of Neurology, 2020, 267:36-44.

Yuan et al., "Neurofilaments and Neurofilament Proteins in Health and Disease," Cold Spring Harb Persepct Biol., Apr. 2017, 9:a018309:1-24.

Kharkevich, *Pharmacology*, 10th ed., GEOTAR Media, 2010-908 p., p. 73, 6 pages (with English Translation).

Verde et al., "Neurofilament light chain in serum for the diagnosis of amyotrophic lateral sclerosis," J. Neurol. Neurosurg. Psychiatry, Feb. 2018,90(2):157-164.

Dalla Costa et al., "Prognostic Value of Serum Neurofilaments Inpatients with Clinically Isolated Syndromes," Neurology, Jan. 2019, 92(7):e733-e741.

Dalla Costa et al., "Serum Neurofilament Light Chain Levels are Increased at the Onset of PML in Natalizumab Treated MS Patients," Poster, presented at the 70th Annual Meeting of the American Academy of Neurology, Los Angeles, California, Apr. 21-27, 2018, 1 page.

Dalla Costa et al., "Serum Neurofilament Light Chain Levels are Increased at the Onset of PML in Natalizumab-treated MS Patients," Abstract, presented at the 4th Congress of the European-Academy-Of-Neurology, Lisbon, Portugal, Jun. 16-19, 2018; European Journal of Neurology, Jun. 2018, 25(Suppl. 2):327, 1 page.

Xunming, "The first FDA Approved by the United States Treatment of Spinal Muscular Atrophy Symptomatic Medications Spinraza (nusinersen)," Journal of Guangdong Pharmaceutical University, Feb. 25, 2017, 46:33, 2 pages (with Machine Translation).

Costa et al., "Prognostic Value of Serum Neurofilaments Inpatients with Clinically Isolated Syndromes", Neurology, Jan. 2019, 92(7):e733-e741.

Costa et al., "Serum Neurofilament Light Chain Levels are Increased at the Onset of PML in Natalizumab Treated MS Patients", 70th Annual Meeting of the American Academy of Neurology, Apr. 2018, 1 page.

Costa et al., "Serum Neurofilament Light Chain Levels are Increased at the Onset of PML in Natalizumab-Treated MS Patients", 4th Congress of the European Academy of Neurology (European Journal of Neurology), Jun. 2018, p. 327.

Fitzner et al., "Molecular Biomarkers in Cerebrospinal Fluid of Multiple Sclerosis Patients", Autoimmunity Reviews, Oct. 2015, 14(10):903-913.

PCT International Preliminary Report on Patentability in International Appln. No. PCT/US2020/017600, dated Aug. 26, 2021, 8 pages.

PCT International Search Report and Written Opinion in International Appln. No. PCT/US2020/017600, dated May 26, 2020, 15 pages.

(56) References Cited

OTHER PUBLICATIONS

Bacioglu et al., "Correction: Update—Neurofilament Light Chain in Blood as CSF as Marker of Disease Progression in Mouse Models and in Neurodegenerative Diseases, " Neuron, Jul. 20, 2016, 91(2):494-496.

ClevelandClinic.org [online], "PML Diagnosis & Management," available on or before Aug. 7, 2020, via internet archive: Wayback Machine URL <https://web.archive.org/web/20200807185742/https://my.clevelandclinic.org/departments/neurological/depts/multiple-sclerosis/ms-approaches/pml-diagnosis-management>, retrieved on May 12, 2025, retrieved from URL <https://my.clevelandclinic.org/departments/neurological/depts/multiple-sclerosis/ms-approaches/pml-diagnosis-management>, 7 pages.

ClevelandClinic.org [online], "Safety Monitoring for Multiple Sclerosis Patients on Disease Modifying Therapies," available on or before Jun. 2, 2023, via internet archive: Wayback Machine URL <https://web.archive.org/web/20230602060148/https://my.clevelandclinic.org/departments/neurological/depts/multiple-sclerosis/ms-approaches/safety-monitoring-multiple-sclerosis-patients-disease-modifying-therapies>, retrieved on May 12, 2025, retrieved from URL <https://my.clevelandclinic.org/departments/neurological/depts/multiple-sclerosis/ms-approaches/safety-monitoring-multiple-sclerosis-patients-disease-modifying-therapies>, 5 pages.

Dalla Costa et al., "Serum Neurofilament Light Chain Levels are Increased at the Onset of PML in Natalizumab Treated MS Patients," Multiple Sclerosis Journal, Oct. 2017, 23(S3):368-369.

U.S. Appl. No. 16/963,914, 20210041459, U.S. Pat. No. 11,474,113, filed Jul. 22, 2020, Farwell.

U.S. Appl. No. 17/819,742, filed Aug. 15, 2022, Farwell.

U.S. Appl. No. 17/299,660, 20220034907, filed Jun. 3, 2021, Ferguson.

* cited by examiner

BIOMARKERS OF PROGRESSIVE MULTIFOCAL LEUKOENCEPHALOPATHY

CROSS-REFERENCE TO RELATED APPLICATIONS

This application is the National Stage of International Application No. PCT/US2020/017600, filed on Feb. 11, 2020, which claims priority to U.S. Provisional Application No. 62/804,701, filed Feb. 12, 2019. The content of the foregoing applications is incorporated by reference herein in their-its entirety.

TECHNICAL FIELD

This disclosure relates generally to biomarkers of progressive multifocal leukoencephalopathy.

BACKGROUND

Progressive multifocal leukoencephalopathy (PML) is a rare demyelinating disease caused by John Cunningham (JC) virus and is often fatal. JC virus is a ubiquitous polyomavirus, and it is estimated that 60 to 80% of the human population has been exposed to JC virus (Walker et al. (1983) *Prog. Clin. Bio. Res.* 105:99-106; Pfister et al. (2001) *J. Virol.* 75(12):5672-6). The virus remains quiescent and does not frequently cause disease in subjects having normal immune systems. However, PML emerges in immune-compromised subjects when JC virus infects and kills oligodendrocytes in the brain. PML was initially described in transplant patients, is apparent in ~5.0% of the AIDS population, and has emerged as a complication of treatment with immune-modulating agents (Berger et al. (1998) *J. Neurovirol.* 4(1):59-68; Koralnik (2004) *Curr. Opin. Neurol.* 17(3):365-70). Identification of a subject as being likely or unlikely to develop PML is important for optimal patient management.

SUMMARY

Neurofilaments are a major component of the neuronal cytoskeleton, particularly in axons where they are essential for growth and maintenance. This disclosure is based, at least in part, on the finding that neurofilament levels serve as effective biomarkers for progressive multifocal leukoencephalopathy (PML).

In one aspect, the disclosure features a method of reducing the occurrence or severity of progressive multifocal leukoencephalopathy (PML) during immunomodulator therapy, the method comprising:

administering multiple doses of an immunomodulator to a human subject at a dosing interval over a period of at least six months;

measuring a first neurofilament level in a first biological sample obtained from the human subject at least six months (e.g., at least nine months, at least one year, or at least 18 months) after initiation of administration of multiple doses of the immunomodulator at the dosing interval;

measuring a second neurofilament level in a second biological sample obtained from the human subject after continued administration of the immunomodulator at the dosing interval, wherein the second biological sample is obtained from the human subject at least six months after the first biological sample is obtained from the human subject, and wherein the second neurofilament level is increased by at least 50% as compared to the first neurofilament level; and assessing the human subject for an indicator of PML.

In some embodiments, the method comprises:

administering multiple doses of natalizumab to a human subject that has multiple sclerosis at a dosing interval over a period of at least six months;

measuring a first neurofilament level in a first biological sample obtained from the human subject at least six months (e.g., at least nine months, at least one year, or at least 18 months) after initiation of administration of multiple doses of natalizumab at the dosing interval;

measuring a second neurofilament level in a second biological sample obtained from the human subject after continued administration of natalizumab at the dosing interval, wherein the second biological sample is obtained from the human subject at least six months after the first biological sample is obtained from the human subject, and wherein the second neurofilament level is increased by at least 50% as compared to the first neurofilament level; and assessing the human subject for an indicator of PML.

In some embodiments, the indicator of PML is a brain scan (e.g., a magnetic resonance imaging (MRI) scan) indicating lesions consistent with PML.

In some embodiments, the indicator of PML is detection of John Cunningham (JC) virus (e.g., JC virus DNA) in a sample (e.g., a cerebrospinal fluid sample) obtained from the human subject.

In some embodiments, the indicator of PML is a brain scan indicating lesions consistent with PML and detection of JC virus (e.g., JC virus DNA) in a sample (e.g., a cerebrospinal fluid sample) obtained from the human subject.

In some embodiments, the indicator of PML is a cognitive assessment test.

In some embodiments, the second biological sample is obtained from the human subject at least one year (e.g., at least 1.5 years, at least two years, at least 2.5 years, at least three years, at least 3.5 years, or at least four years) after the first biological sample is obtained from the human subject.

In some embodiments, the second neurofilament level is increased by at least 100% (e.g., at least 200%, at least 300%, at least 400%, at least 500% at least 600%, or at least 700%) as compared to the first neurofilament level.

In some embodiments, the neurofilament level in the human subject is measured at least once every 6 months (e.g., at least once every 5 months, at least once every 4 months, at least once every 3 months, at least once every 2 months, at least once every month, at least once every 4 weeks, at least once every 3 weeks, at least once every 2 weeks, or at least once every week) between the time when the first biological sample is obtained from the human subject and the time when the second biological sample is obtained from the human subject.

In some embodiments, during the period between the time when the first biological sample is obtained from the human subject and the time when the second biological sample is obtained from the human subject, the neurofilament level is measured on the same days that the immunomodulator is administered to the human subject.

In some embodiments, after measuring the second neurofilament level, the systemic level of the immunomodulator (e.g., natalizumab) in the human subject is actively reduced (e.g., actively reduced by plasma exchange).

In some embodiments, after measuring the second neurofilament level, the amount and/or frequency of the immunomodulator administered to the human subject is reduced as compared to the doses administered at the dosing interval prior to measuring the second neurofilament level.

In some embodiments, after measuring the second neurofilament level, treatment of the human subject with the immunomodulator is discontinued for a period of at least six months.

In some embodiments, after measuring the second neurofilament level, treatment of the human subject with the immunomodulator is permanently discontinued.

In some embodiments, after measuring the second neurofilament level, the human subject is administered an immune reconstituting agent (e.g., a hemopoietic growth factor such as granulocyte colony-stimulating factor or granulocyte-macrophage colony-stimulating factor).

In some embodiments, the second neurofilament level is above 8 pg/mL.

In some embodiments, the second neurofilament level is at least 16 pg/mL (e.g., at least 20 pg/mL, at least 25 pg/mL, at least 30 pg/mL, at least 35 pg/mL, at least 40 pg/mL, at least 45 pg/mL, or at least 50 pg/mL).

In some embodiments, the second neurofilament level is above the 80th percentile of normative neurofilament levels adjusted for age.

In some embodiments, at the time the second biological sample is obtained from the human subject, the human subject has not been diagnosed as having clinical symptoms of PML.

In some embodiments, the human subject has an autoimmune disorder (e.g., multiple sclerosis, psoriasis, systemic lupus erythematosus, Crohn's disease, or rheumatoid arthritis).

In some embodiments, the human subject has received an organ, cell, or tissue transplant (e.g., a transplant of a kidney, a heart, a lung, a liver, intestinal tissue, skin, muscle, a nerve, stem cells, or bone marrow).

In some embodiments, the human subject has a cancer.

In some embodiments, the immunomodulator is azathioprine, cyclosporine, cyclophosphamide, efalizumab, leflunomide, methotrexate, mycophenolate mofetil, natalizumab, rituximab, tacrolimus sirolimus, methotrexate, infliximab, ibritumomab, fingolimod, glucocorticoid, a corticosteroid, dimethyl fumarate, belatacept, interferon beta-la (e.g., Avonex), or a chemotherapeutic agent.

In some embodiments, the human subject has multiple sclerosis.

In some embodiments, the immunomodulator is natalizumab.

In some embodiments, the human subject has multiple sclerosis and the immunomodulator is natalizumab.

In another aspect, the disclosure features a method of monitoring for asymptomatic progressive multifocal leukoencephalopathy (PML) during immunomodulator (e.g., natalizumab) therapy, the method comprising administering multiple doses of an immunomodulator to a human subject (e.g., a subject that has multiple sclerosis) over a period of treatment of at least one year, wherein a neurofilament level is measured in a biological sample obtained from the human subject at least once every 6 months during the period of treatment.

In some embodiments, the immunomodulator is administered to the human subject at least once every 3 months (e.g., at least once every 2 months, at least once every month, at least once every 4 weeks, at least once every 3 weeks, at least once every 2 weeks, or at least once every week) during the period of treatment.

In some embodiments, the neurofilament level is measured in a biological sample obtained from the human subject at least once every 4 weeks (e.g., at least once every 3 weeks, at least once every 2 weeks, or at least once every week) during the period of treatment.

In some embodiments, the neurofilament level is measured on the same days that the immunomodulator is administered to the human subject.

In some embodiments, the human subject has multiple sclerosis.

In some embodiments, the immunomodulator is natalizumab.

In some embodiments, the human subject has multiple sclerosis and the immunomodulator is natalizumab.

In another aspect, the disclosure features a method of identifying the onset of asymptomatic progressive multifocal leukoencephalopathy (PML) during immunomodulator (e.g., natalizumab) therapy, the method comprising:

measuring a first neurofilament level in a first biological sample obtained from a human subject (e.g., a subject that has multiple sclerosis) at least six months after initiation of administration of multiple doses of an immunomodulator at a dosing interval;

measuring a second neurofilament level in a second biological sample obtained from the human subject after continued administration of the immunomodulator at the dosing interval, wherein the second biological sample is obtained from the human subject at least six months after the first biological sample is obtained from the human subject; and comparing the first neurofilament level in the first biological sample to the second neurofilament level in the second biological sample, wherein an increase of the second neurofilament level by at least 50% as compared to the first neurofilament level indicates that the human subject has asymptomatic PML.

In some embodiments, the human subject has multiple sclerosis.

In some embodiments, the immunomodulator is natalizumab.

In some embodiments, the human subject has multiple sclerosis and the immunomodulator is natalizumab.

In another aspect, the disclosure features a method for early identification of progressive multifocal leukoencephalopathy (PML) in an immunocompromised human subject, the method comprising:

measuring a first neurofilament level in a first biological sample obtained from the human subject;

measuring a second neurofilament level in a second biological sample obtained from the human subject, wherein the second biological sample is obtained from the human subject at least six months after the first biological sample is obtained from the human subject, and wherein the second neurofilament level is increased by at least 50% as compared to the first neurofilament level; and assessing the human subject for an indicator of PML.

In some embodiments, the immunocompromised human subject has an human immunodeficiency virus (HIV) infection.

In some embodiments, the immunocompromised human subject has an autoimmune disease.

In some embodiments, the immunocompromised human subject has a cancer.

These embodiments apply to any of the above aspects. In certain instances, the neurofilament is a neurofilament light chain (NF-L). In certain instances, the neurofilament is a neurofilament heavy chain (e.g., phosphorylated NF-H). In certain instances, the neurofilament is a neurofilament medium/intermediate chain. In certain instances, the neurofilament is internexin. In certain instances, the neurofilament is peripherin. In certain instances, the biological sample is blood, serum, plasma, cerebrospinal fluid, saliva, or tears. In some instances, NF-L is detected using a polyclonal anti-NF-L antibody. In some instances, NF-L is detected using a monoclonal anti-NF-L antibody. some instances, NF-L is detected using a single molecule array (SIMOA) method described in Disanto et al., Ann. Neurol. 81(6): 857-870, 2017. The SIMOA assay (particularly called the Simoa NF-light Advantage kit) is commercially available from Quanterix Corp. (Lexington, MA, USA).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description and from the claims.

DETAILED DESCRIPTION

Figure 1:
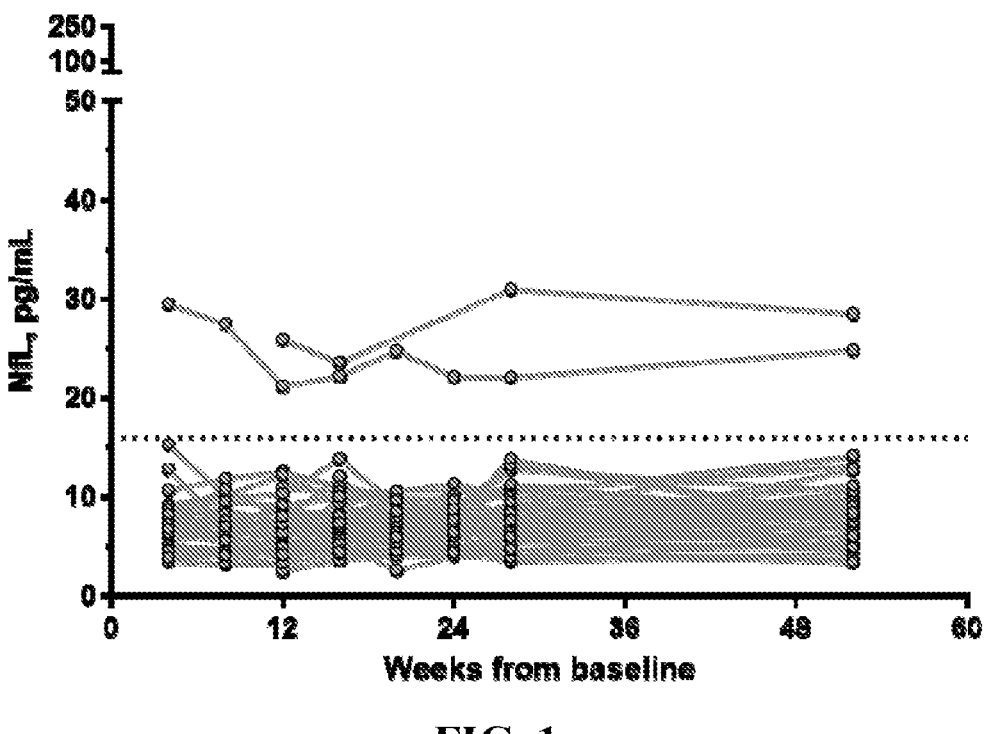
FIG. 1 is a graph depicting sNfL concentrations over time in natalizumab-treated non-PML patients.

This disclosure is based, in part, on the surprising finding that elevated neurofilament (NF) levels can serve as an effective biomarker for PML prior to the onset of clinical symptoms.
Risk Factors for PML JC virus causes PML in a subset of immune-compromised subjects, including those that have been treated with immunomodulators (e.g., immunosuppressants). The methods described herein allow for the identification of subjects at heightened risk for developing PML.

In some embodiments, the subject has an autoimmune disease, which can be, for example, multiple sclerosis, rheumatoid arthritis, insulin-dependent diabetes mellitus (IDDM), Crohn's disease, psoriasis, Behçet's disease, ankylosing spondylitis, systemic lupus erythematosus, or muscular dystrophy. Autoimmune diseases are frequently treated with any of a variety of immunomodulators (e.g., immunosuppressants).

In other embodiments, the subject is an organ, cell, or tissue transplant recipient. The transplant can be allogeneic (e.g., where a human patient is a recipient of a graft from an HLA non-identical human donor) or xenogeneic (e.g., where a human patient is a recipient of a graft from donor of a species other than human, e.g., a pig or a non-human primate). The organ, cell, or tissue can be, for example, a kidney, a heart, a lung, a liver, an intestinal tissue, a skin, a muscle, a nerve, a stem cell, or a bone marrow graft. Transplant patients take medications to suppress their immune system as an anti-rejection measure.

In some embodiments of any of the methods described herein, the subject has a cancer, e.g., leukemia, lymphoma, multiple myeloma, lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, or bladder cancer. Cancers are frequently treated with any of a variety of immunomodulators (e.g., immunosuppressants).

In other embodiments, the subject has an immunodeficiency disease, wherein the immunodeficiency disease is a primary immune disease or an acquired immune disease. The acquired immune disease can be human immunodeficiency virus 1 (HIV-1) or human immunodeficiency virus 2 (HIV-2) acquired immunodeficiency syndrome (AIDS). An immunodeficient subject has a compromised or entirely absent immune system, lacking the ability to fight infectious disease. Most cases of immunodeficiency are acquired ("secondary"), but some people are born with defects in the immune system, or primary immunodeficiency. A subject who has an immunodeficiency of any kind is said to be immunocompromised. An immunocompromised subject may be particularly vulnerable to opportunistic infections, in addition to infections that affect subjects with normal immune systems.

The subjects can also be those undergoing any of a variety of immunomodulatory (e.g., immunosuppressive) therapies. Thus, for example, cancer patients can be those being treated with one or more chemotherapeutic agents one or more forms of ionizing radiation, one or more immunotherapy agents, and/or one or more hyperthermotherapy agents. The one or more forms of ionizing radiation can be gamma-irradiation, X-irradiation, or beta-irradiation. In this regard, a subject can be one that has been exposed to highly immunosuppressive doses of ionizing radiation. Patients receiving, for example, stem cell or bone marrow transplants can also have been exposed to high doses of ionizing radiation.

The one or more chemotherapeutic agents can be selected from the group consisting of cisplatin, carboplatin, procarbazine, mechlorethamine, cyclophosphamide, camptothecin, adriamycin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, transplatinum, 5-flurouracil, vincristin, vinblastin, methotrexate, and an analog of any of the aforementioned.

Subjects can also be autoimmune disease patients or transplant patients being treated with any of a variety of immunomodulatory (e.g., immunosuppressive) agents. Such immunomodulatory (e.g., immunosuppressive) agents include antibodies. The antibodies can be polyclonal antibodies, monoclonal antibodies (e.g., mouse or human monoclonal antibodies), recombinant chimeric or humanized antibodies. These types of antibodies are described in greater detail in, for example, Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., U.S. Pat. No. 4,816,567; Cabilly et al., European Patent Application 125,023; Better et al. (1988) *Science* 240:1041-43; Liu et al. (1987) *J. Immunol.* 139: 3521-26; Sun et al. (1987) *PNAS* 84:214-18; Nishimura et al. (1987) *Canc. Res.* 47:999-1005; Wood et al. (1985) *Nature* 314:446-49; Shaw et al. (1988) *J. Natl. Cancer Inst.* 80:1553-59; Morrison (1985) *Science* 229:1202-07; Oi et al. (1986) *BioTechniques* 4:214; Winter, U.S. Pat. No. 5,225, 539; Jones et al. (1986) *Nature* 321:552-25; Veroeyan et al. (1988) *Science* 239:1534; and Beidler et al. (1988) *J. Immunol.* 141:4053-60, the disclosures of which are incorporated herein by reference in their entirety. Immunomodulatory (e.g., immunosuppressive) agents can also be antigen-binding antibody fragments. Antibody fragments that contain the binding domain of the molecule can be generated by known techniques. For example: F(ab')₂ fragments can be produced by pepsin digestion of antibody molecules; and Fab fragments can be generated by reducing the disulfide bridges of F(ab')₂ fragments or by treating antibody molecules with papain and a reducing agent. See, e.g., National Institutes of Health, 1 *Current Protocols In Immunology*, Coligan et al., ed. 2.8, 2.10 (Wiley Interscience, 1991) the disclosure of which is incorporated herein by reference in its entirety. Single chain Fv (scFv) fragments can be produced, for example, as described in U.S. Pat. No. 4,642,334, the disclosure of which is incorporated herein by reference in its entirety. Examples of appropriate antibodies include an anti-α4-integrin antibody (e.g., natalizumab), an anti-TNFα antibody (e.g., infliximab, adalimumab, and etanercept), an anti-CD20 antibody (e.g., rituximab and ocrelizumab), an anti-CD11a antibody (e.g., efalizumab), an anti-CD3 antibody (e.g., muromonab), and anti-IL-2 antibodies (e.g., basiliximab and daclizumab).

Immunomodulatory (e.g., immunosuppressive) agents also include small molecules. Small molecule immunomodulatory (e.g., immunosuppressive) agents can be, for example, sirolimus, tacrolimus, ciclosporin, fingolimod, myriocin, prednisone, prednisolone, methylprednisolone, dexamethasone, betamethasone, triamcinolone, beclometasone, fludrocortisones, and an analog of any of the aforementioned.

Biomarkers for PML

This disclosure illustrates the use of neurofilament levels as a novel biomarker for PML prior to the onset of clinical symptoms. Neurofilaments (NFs) are the predominant cystokeletal element in nerve cells and play a role not only in conferring mechanical stability but also in determining axonal caliber. Human NFs are composed of three protein subunits, NF-L, NF-M, and NF-H. These proteins share the same basic architecture as other intermediate filament subunit proteins. Neurofilaments in the mammalian nervous system also contain the protein internexin and neurofilaments in the peripheral nervous system can also contain the protein peripherin. Thus, as used herein, by "a neurofilament protein" is meant neurofilament heavy chain (NF-H), neurofilament medium/intermediate chain (NF-M), neurofilament light chain (NF-L), internexin, or peripherin. The PML biomarker can be one or more of NF-H, NF-M, NF-L, internexin, and peripherin. In certain instances, the PML biomarker is a phosphorylated NF-H (pNF-H). In certain instances, the PML biomarker is a phosphorylated NF-L. The levels of the neurofilament biomarker can be assessed using RNA (e.g., mRNA) or protein.

The amino acid sequences of human NF-H are provided in SEQ ID NO:1 and SEQ ID NO:5 and in Lees et al., *EMBO*

8

*J,* 7(7); 1947-1955 (1988), UniProtKB—P12036, NCBI Reference Sequence: NG 008404.1, NCBI Reference Sequence: NP_066554.2.

```
                                              SEQ ID NO: 1
MMSFGGADALLGAPFAPLHGGGSLHYALARKGGAGGTRSAAGSSSGFHS

WTRTSVSSVSASPSRFRGAGAASSTDSLDTLSNGPEGCMVAVATSRSEK

EQLQALNDRFAGYIDKVRQLEAHNRSLEGEAAALRQQQAGRSAMGELYE

REVREMRGAVLRLGAARGQLRLEQEHLLEDIAHVRQRLDDEARQREEAE

AAARALARFAQEAEAARVDLQKKAQALQEECGYLRRHHQEEVGELLGQI

QGSGAAQAQMQAETRDALKCDVTSALREIRAQLEGHAVQSTLQSEEWFR

VRLDRLSEAAKVNTDAMRSAQEEITEYRRQLQARTTELEALKSTKDSLE

RQRSELEDRHQADIASYQEAIQQLDAELRNTKWEMAAQLREYQDLLNVK

MALDIEIAAYRKLLEGEECRIGFGPIPFSLPEGLPKIPSVSTHIKVKSE

EKIKVVEKSEKETVIVEEQTEETQVTEEVTEEEEKEAKEEEGKEEEGGE

EEEAEGGEEETKSPPAEEAASPEKEAKSPVKEEAKSPAEAKSPEKEEAK

SPAEVKSPEKAKSPAKEEAKSPPEAKSPEKEEAKSPAEVKSPEKAKSPA

KEEAKSPAEAKSPEKAKSPVKEEAKSPAEAKSPVKEEAKSPAEVKSPEK

AKSPTKEEAKSPEKAKSPEKAKSPEKEEAKSPEKAKSPVKAEAKSPEKA

KSPVKAEAKSPEKAKSPVKEEAKSPEKAKSPVKEEAKSPEKAKSPVKEE

AKTPEKAKSPVKEEAKSPEKAKSPEKAKTLDVKSPEAKTPAKEEARSPA

DKFPEKAKSPVKEEVKSPEKAKSPLKEDAKAPEKEIPKKEEVKSPVKEE

EKPQEVKVKEPPKKAEEEKAPATPKTEEKKDSKKEEAPKKEAPKPKVEE

KKEPAVEKPKESKVEAKKEEAEDKKKVPTPEKEAPAKVEVKEDAKPKEK

TEVAKKEPDDAKAKEPSKPAEKKEAAPEKKDTKEEKAKKPEEKPKTEAK

AKEDDKTLSKEPSKPKAEKAEKSSSTDQKDSKPPEKATEDKAAKGK

SEQ ID NO: 5
MMSFGGADALLGAPFAPLHGGGSLHYALARKGGAGGTRSAAGSSSG

FHSWTRTSVSSVSASPSRFRGAGAASSTDSLDTLSNGPEGCMVAVA

TSRSEKEQLQALNDRFAGYIDKVRQLEAHNRSLEGEAAALRQQQAG

RSAMGELYEREVREMRGAVLRLGAARGQLRLEQEHLLEDIAHVRQR

LDDEARQREEAEAAARALARFAQEAEAARVDLQKKAQALQEECGYL

RRHHQEEVGELLGQIQGSGAAQAQMQAETRDALKCDVTSALREIRA

QLEGHAVQSTLQSEEWFRVRLDRLSEAAKVNTDAMRSAQEEITEYR

RQLQARTTELEALKSTKDSLERQRSELEDRHQADIASYQEAIQQLD

AELRNTKWEMAAQLREYQDLLNVKMALDIEIAAYRKLLEGEECRIG

FGPIPFSLPEGLPKIPSVSTHIKVKSEEKIKVVEKSEKETVIVEEQ

TEETQVTEEVTEEEEKEAKEEEGKEEEGGEEEEAEGGEEETKSPPA

EEAASPEKEAKSPVKEEAKSPAEAKSPEKEEAKSPAEVKSPEKAKS

PAKEEAKSPPEAKSPEKEEAKSPAEVKSPEKAKSPAKEEAKSPAEA

KSPEKAKSPVKEEAKSPAEAKSPVKEEAKSPAEVKSPEKAKSPTKE

EAKSPEKAKSPEKEEAKSPEKAKSPVKAEAKSPEKAKSPVKAEAKS

PEKAKSPVKEEAKSPEKAKSPVKEEAKSPEKAKSPVKEEAKTPEKA
```

-continued

KSPVKEEAKSPEKAKSPEKAKTLDVKSPEAKTPAKEEARSPADKFP

EKAKSPVKEEVKSPEKAKSPLKEDAKAPEKEIPKKEEVKSPVKEEE

KPQEVKVKEPPKKAEEEKAPATPKTEEKKDSKKEEAPKKEAPKPKV

EEKKEPAVEKPKESKVEAKKEEAEDKKKVPTPEKEAPAKVEVKEDA

KPKEKTEVAKKEPDDAKAKEPSKPAEKKEAAPEKKDTKEEKAKKPE

EKPKTEAKAKEDDKTLSKEPSKPKAEKAEKSSSTDQKDSKPPEKAT

EDKAAKGK

The amino acid sequence of human NF-L is provided in SEQ ID NO:2 and in Julien et al., *Biochimica et Biohysica Acta,* 909:10-20 (1987), UniProtKB-P07196, NCBI Reference Sequence: NP_006149.2, and NCBI Reference Sequence: NG_008492.1.

SEQ ID NO: 2

MSSFSYEPYYSTSYKRRYVETPRVHISSVRSGYSTARSAYSSYSAP

VSSSLSVRRSYSSSSGSLMPSLENLDLSQVAAISNDLKSIRTQEKA

QLQDLNDRFASFIERVHELEQQNKVLEAELLVLRQKHSEPSRFRAL

YEQEIRDLRLAAEDATNEKQALQGEREGLEETLRNLQARYEEEVLS

REDAEGRLMEARKGADEAALARAELEKRIDSLMDEISFLKKVHEEE

IAELQAQIQYAQISVEMDVTKPDLSAALKDIRAQYEKLAAKNMQNA

EEWFKSRFTVLTESAAKNTDAVRAAKDEVSESRRLLKAKTLEIEAC

RGMNEALEKQLQELEDKQNADISAMQDTINKLENELRTTKSEMARY

LKEYQDLLNVKMALDIEIAAYRKLLEGEETRLSFTSVGSITSGYSQ

SSQVFGRSAYGGLQTSSYLMSTRSFPSYYTSHVQEEQIEVEETIEA

AKAEEAKDEPPSEGEAEEEEKDKEEAEEEEAAEEEEEAAKEESEEAK

EEEEGGEGEEGEETKEAEEEEEKKVEGAGEEQAAKKKD

The amino acid sequences of human NF-M are provided in SEQ ID NO:3 and SEQ ID NO:6 and in Myers et al., *EMBO J.,* 6(6):1617-1626 (1987) and in UniProtKB-P07197.

SEQ ID NO: 3

MSYTLDSLGNPSAYRRVTETRSSFSRVSGSPSSGFRSQSWSRGSPS

TVSSSYKRSMLAPRLAYSSAMLSSAESSLDFSQSSSLLNGGSGPGG

DYKLSRSNEKEQLQGLNDRFAGYIEKVHYLEQQNKEIEAEIQALRQ

KQASHAQLGDAYDQEIRELRATLEMVNHEKAQVQLDSDHLEEDIHR

LKERFEEEARLRDDTEAAIRALRKDIEEASLVKVELDKKVQSLQDE

VAFLRSNHEEEVADLLAQIQASHITVERKDYLKTDISTALKEIRSQ

LESHSDQNMHQAEEWFKCRYAKLTEAAEQNKEAIRSAKEEIAEYRR

QLQSKSIELESVRGTKESLERQLSDIEERHNHDLSSYQDTIQQLEN

ELRGTKWEMARHLREYQDLLNVKMALDIEIAAYRKLLEGEETRFST

FAGSITGPLYTHRPPITISSKIQKPKVEAPKLKVQHKFVEEIIEET

KVEDEKSEMEEALTAITEELAVSMKEEKKEAAEEKEEEPEAEEEEV

AAKKSPVKATAPEVKEEEGEKEEEEGQEEEEEEDEGAKSDQAEEGG

SEKEGSSEKEEGEQEEGETEAEAEGEEAEAKEEKKVEEKSEEVATK

-continued

EELVADAKVEKPEKAKSPVPKSPVEEKGKSPVPKSPVEEKGKSPVP

KSPVEEKGKSPVPKSPVEEKGKSPVSKSPVEEKAKSPVPKSPVEEA

KSKAEVGKGEQKEEEEKEVKEAPKEEKVEKKEEKPKDVPEKKKAES

PVKEEAVAEVVTITKSVKVHLEKETKEEGKPLQQEKEKEKAGGEGG

SEEEGSDKGAKGSRKEDIAVNGEVEGKEEVEQETKEKGSGREEEKG

VVTNGLDLSPADEKKGGDKSEEKVVVTKTVEKITSEGGDGATKYIT

KSVTVTQKVEEHEETFEEKLVSTKKVEKVTSHAIVKEVTQSD

SEQ ID NO: 6

MARHLREYQDLLNVKMALDIEIAAYRKLLEGEETRFSTFAGSITGP

LYTHRPPITISSKIQKPKVEAPKLKVQHKFVEEIIEETKVEDEKSE

MEEALTAITEELAVSMKEEKKEAAEEKEEEPEAEEEEVAAKKSPVK

ATAPEVKEEEGEKEEEEGQEEEEEEDEGAKSDQAEEGGSEKEGSSE

KEEGEQEEGETEAEAEGEEAEAKEEKKVEEKSEEVATKEELVADAK

VEKPEKAKSPVPKSPVEEKGKSPVPKSPVEEKGKSPVPKSPVEEKG

KSPVPKSPVEEKGKSPVSKSPVEEKAKSPVPKSPVEEAKSKAEVGK

GEQKEEEEKEVKEAPKEEKVEKKEEKPKDVPEKKKAESPVKEEAVA

EVVTITKSVKVHLEKETKEEGKPLQQEKEKEKAGGEGGSEEEGSDK

GAKGSRKEDIAVNGEVEGKEEVEQETKEKGSGREEEKGVVTNGLDL

SPADEKKGGDKSEEKVVVTKTVEKITSEGGDGATKYITKSVTVTQK

VEEHEETFEEKLVSTKKVEKVTSHAIVKEVTQSD

The amino acid sequence of human internexin is provided in SEQ ID NO:7.

SEQ ID NO: 7

MSFGSEHYLCSSSSYRKVFGDGSRLSARLSGAGGAGGFRSQSLSRS

NVASSAACSSASSLGLGLAYRRPPASDGLDLSQAAARTNEYKIIRT

NEKEQLQGLNDRFAVFIEKVHQLETQNRALEAELAALRQRHAEPSR

VGELFQRELRDLRAQLEEASSARSQALLERDGLAEEVQRLRARCEE

ESRGREGAERALKAQQRDVDGATLARLDLEKKVESLLDELAFVRQV

HDEEVAELLATLQASSQAAAEVDVTVAKPDLTSALREIRAQYESLA

AKNLQSAEEWYKSKFANLNEQAARSTEAIRASREEIHEYRRQLQAR

TIEIEGLRGANESLERQILELEERHSAEVAGYQDSIGQLENDLRNT

KSEMARHLREYQDLLNVKMALDIEIAAYRKLLEGEETRFSTSGLSI

SGLNPLPNPSYLLPPRILSATTSKVSSTGLSLKKEEEEEEASKVAS

KKTSQIGESFEEILEETVISTKKTEKSNIEETTISSQKI

The amino acid sequence of human peripherin is provided in SEQ ID NO:8.

SEQ ID NO: 8

MSHHPSGLRAGFSSTSYRRTFGPPPSLSPGAFSYSSSSRFSSSRLL

GSASPSSSVRLGSFRSPRAGAGALLRLPSERLDFSMAEALNQEFLA

TRSNEKQELQELNDRFANFIEKVRFLEQQNAALRGELSQARGQEPA

RADQLCQQELRELRRELELLGRERDRVQVERDGLAEDLAALKQRLE

-continued

```
EETRKREDAEHNLVLFRKDVDDATLSRLELERKIESLMDEIEFLKK

LHEEELRDLQVSVESQQVQQVEVEATVKPELTAALRDIRAQYESIA

AKNLQEAEEWYKSKYADLSDAANRNHEALRQAKQEMNESRRQIQSL

TCEVDGLRGTNEALLRQLRELEEQFALEAGGYQAGAARLEEELRQL

KEEMARHLREYQELLNVKMALDIEIATYRKLLEGEESRISVPVHSF

ASLNIKTTVPEVEPPQDSHSRKTVLIKTIETRNGEVVTESQKEQRS

ELDKSSAHSY
```

In certain instances, the level of NF (e.g., NF-L) is used in combination with one or more other PML biomarkers.
Diagnosing PML The disclosure features methods of diagnosing whether a subject receiving an immunomodulatory (e.g., immunosuppressive) therapy is likely to develop PML. The method involves measuring a neurofilament level in a biological sample obtained from the subject. PML (e.g., prior to onset of symptoms) is diagnosed if the neurofilament level in the subject is higher than a control level.

In some instances, the method involves measuring a NF-L level in the biological sample obtained from the subject. In some instances, the method involves measuring a NF-H level in the biological sample obtained from the subject. In some instances, the method involves measuring a pNF-H level in the biological sample obtained from the subject. In some instances, the method involves measuring a NF-M level in the biological sample obtained from the subject.

The biological sample can be e.g., blood, serum, plasma, cerebrospinal fluid, saliva, or tears. In some instances, the biological sample is plasma. In some instances, the biological sample is serum.

In some instances, the NF level is measured by assessing the level of NF RNA (e.g., mRNA) in the biological sample.

In some instances, the NF level is measured by assessing the level of an NF protein (NF-H, NF-M, or NF-L protein) in the biological sample. In certain instances, the NF protein is pNF-H. The concentration of the protein or proteins of interest can be measured using any method known in the art such as an immunological assay. Non-limiting examples of such methods include enzyme immunoassay, radioimmunoassay, chemiluminescent immunoassay, electrochemiluminescence immunoassay, latex turbidimetric immunoassay, latex photometric immunoassay, immuno-chromatographic assay, and western blotting. In certain embodiments, the concentration of the protein or proteins of interest is measured by mass spectrometry.

In some embodiments, the neurofilament level (e.g., NF-L) in the biological sample is above a control level. In some embodiments, the neurofilament level in the biological sample is above 8 pg/mL. In some embodiments, the neurofilament light chain level (e.g., in serum) is above 8 pg/mL as measured using the Simoa NF-light Advantage kit from Quanterix Corp (Lexington, MA). In some embodiments the neurofilament level in the biological sample is at least 16 pg/mL (e.g., at least 16 pg/ml neurofilament light chain in serum as measured using the Simoa NF-light Advantage kit from Quanterix Corp.). In some embodiments the neurofilament level in the biological sample is at least 20 pg/mL (e.g., at least 20 pg/ml neurofilament light chain in serum as measured using the Simoa NF-light Advantage kit from Quanterix Corp.). In some embodiments the neurofilament level in the biological sample is at least 25 pg/mL (e.g., at least 25 pg/ml neurofilament light chain in serum as measured using the Simoa NF-light Advantage kit from Quanterix Corp.). In some embodiments, the neurofilament level in the biological sample is at least 30 pg/mL (e.g., at least 30 pg/ml neurofilament light chain in serum as measured using the Simoa NF-light Advantage kit from Quanterix Corp.). In some embodiments, the neurofilament level in the biological sample is at least 35 pg/mL (e.g., at least 35 pg/ml neurofilament light chain in serum as measured using the Simoa NF-light Advantage kit from Quanterix Corp.). In some embodiments, the neurofilament level in the biological sample is at least 40 pg/mL (e.g., at least 40 pg/ml neurofilament light chain in serum as measured using the Simoa NF-light Advantage kit from Quanterix Corp.). In some embodiments, the neurofilament level in the biological sample is at least 45 pg/mL (e.g., at least 45 pg/ml neurofilament light chain in serum as measured using the Simoa NF-light Advantage kit from Quanterix Corp.). In some embodiments, the neurofilament level in the biological sample is a at least 50 pg/mL (e.g., at least 50 pg/ml neurofilament light chain in serum as measured using the Simoa NF-light Advantage kit from Quanterix Corp.).
Controls As described above, the methods of the present disclosure can involve, measuring the expression level (e.g., mRNA or protein concentration) of one or more NF genes or proteins in a biological sample from a subject (e.g., a presymptomatic human subject), wherein the expression level of one or more of the NF genes or proteins, compared to a control, predicts whether a subject is likely to develop PML.

In certain embodiments, when diagnosing whether a subject is likely to develop PML, where the concentration of a NF protein (e.g., NF-L) in a biological sample from a subject is higher than the control, the subject is identified as likely to develop PML. In this context, the term "control" includes a sample (from the same source—e.g., blood, plasma, serum, CSF, saliva, or tears) obtained in the past from the subject and used as a reference for future comparisons to test samples taken the subject for whom PML is to be predicted. The "control" expression level/concentration for a particular NF protein may also be pre-established by an analysis of protein expression in one or more (e.g., two, three, four, five, six, seven, eight, nine, 10, 15, 20, 25, 30, 35, or 40 or more) human subjects of similar age that did not develop PML. This pre-established reference value (which may be an average or median expression level/concentration taken from multiple subjects that did not develop PML) may then be used for the "control" concentration/expression level of the protein or nucleic acid in the comparison with the test sample. In such a comparison, the subject is predicted to is likely to develop PML if the expression level of the NF being analyzed is higher than the pre-established reference.

The "control" concentration for a particular protein (e.g., NF-L) in a particular biological fluid, cell type, or tissue may alternatively be pre-established by an analysis of gene expression in one or more subjects that have not developed PML. This pre-established reference value (which may be an average or median expression level taken from multiple subjects that have responded to the therapy) may then be used as the "control" expression level in the comparison with the test sample. In such a comparison, the subject is predicted to be unlikely to develop PML if the concentration of the protein being analyzed is the same as, or comparable to (at least 85% but less than 100% of), the pre-established reference.

In certain embodiments, the "control" is a pre-determined cut-off value.

In some embodiments, the methods described herein include determining if the concentration of a NF protein(s) of interest falls above or below a predetermined cut-off value.

A cut-off value is typically a concentration of a protein above or below which is considered predictive of something—e.g., likely to develop PML; or responsiveness of a subject to a therapy of interest. Thus, in accordance with the methods described herein, a reference concentration of a NF protein (e.g., NF-L) is identified as a cut-off value, above or below of which is predictive of a subject being likely to develop PML. Some cut-off values are not absolute in that clinical correlations can still remain significant over a range of values on either side of the cutoff; however, it is possible to select an optimal cut-off value (e.g. varying H-scores) of concentration of NF proteins for a particular sample type. Cut-off values determined for use in the methods described herein can be compared with, e.g., published ranges of NF concentrations, but can be individualized to the methodology used and patient population. It is understood that improvements in optimal cut-off values could be determined depending on the sophistication of statistical methods used and on the number and source of samples used to determine reference level values for the different proteins, genes, and sample types. Therefore, established cut-off values can be adjusted up or down, on the basis of periodic re-evaluations or changes in methodology or population distribution.

The reference concentration of one or more NF proteins can be determined by a variety of methods. The reference level can be determined by comparison of the concentration of a NF protein of interest in, e.g., populations of subjects (e.g., patients) that did not develop PML or that did develop PML. This can be accomplished, for example, by histogram analysis, in which an entire cohort of patients is graphically presented, wherein a first axis represents the concentration of a protein of interest and a second axis represents the number of subjects in the cohort whose sample contain one or more concentrations. Determination of the reference concentration of a protein can then be made based on an amount or concentration which best distinguishes these separate groups. The reference level can be a single number, equally applicable to every subject, or the reference level can vary, according to specific subpopulations of subjects. For example, older subjects can have a different reference level than younger subjects.

The pre-established cut-off value can be a NF protein concentration (e.g., NF-L) that is determined based on receiver operating characteristic (ROC) analysis. In one embodiment, the NF protein concentration is determined based on ROC analysis predicting that a subject will develop PML with a positive predictive value, wherein a concentration of a protein of interest (e.g., NF-L) equal to or below the pre-established cut-off value is a low concentration of the protein of interest and a value higher than the pre-established cut-off value is a high concentration of the protein of interest. The positive predictive value is the proportion of positive test results that are true positives; it reflects the probability that a positive test reflects the underlying condition being tested for. Methods of constructing ROC curves and determining positive predictive values are well known in the art.

In another embodiment, the pre-established cut-off value can be a NF protein concentration that is determined based on simulation models predicting that a subject will develop PML, and wherein a concentration of the protein of interest (e.g., NF-L) equal to or below the pre-established cut-off value is a low concentration of the protein of interest and a value higher than the pre-established cut-off value is a high concentration of the protein of interest.

Biological Samples

Suitable biological samples for the methods described herein include any biological fluid, cell, tissue, or fraction thereof, which includes analyte biomolecules of interest such as NF protein or nucleic acid (e.g., RNA (mRNA)). A biological sample can be, for example, a specimen obtained from a human subject or can be derived from such a subject. For example, a sample can be a tissue section obtained by biopsy, archived biological fluid, or cells that are placed in or adapted to tissue culture. In some instances, a biological sample is a biological fluid such as blood, plasma, serum, cerebrospinal fluid (CSF), saliva, tears, urine, or such a sample absorbed onto a substrate (e.g., glass, polymer, paper). A biological sample can be further fractionated, if desired, to a fraction containing particular cell types. For example, a blood sample can be fractionated into serum or into fractions containing particular types of blood cells such as red blood cells or white blood cells (leukocytes). If desired, a sample can be a combination of samples from a subject such as a combination of a tissue and fluid sample.

The biological samples can be obtained from a subject receiving an immunomodulator therapy. In certain embodiments, the subject is an immunocompromised subject. In certain embodiments, the subject has no clinical symptoms of PML.

Any suitable methods for obtaining the biological samples can be employed, although exemplary methods include, e.g., phlebotomy, fine needle aspirate biopsy procedure. Samples can also be collected, e.g., by microdissection (e.g., laser capture microdissection (LCM) or laser microdissection (LMD)).

Methods for obtaining and/or storing samples that preserve the activity or integrity of molecules (e.g., nucleic acids or proteins) in the sample are well known to those skilled in the art. For example, a biological sample can be further contacted with one or more additional agents such as buffers and/or inhibitors, including one or more of nuclease, protease, and phosphatase inhibitors, which preserve or minimize changes in the molecules (e.g., nucleic acids or proteins) in the sample. Such inhibitors include, for example, chelators such as ethylenediamine tetraacetic acid (EDTA), ethylene glycol bis(P-aminoethyl ether) N,N,N1, N1-tetraacetic acid (EGTA), protease inhibitors such as phenylmethylsulfonyl fluoride (PMSF), aprotinin, leupeptin, antipain, and the like, and phosphatase inhibitors such as phosphate, sodium fluoride, vanadate, and the like. Suitable buffers and conditions for isolating molecules are well known to those skilled in the art and can be varied depending, for example, on the type of molecule in the sample to be characterized (see, e.g., Ausubel et al. Current Protocols in Molecular Biology (Supplement 47), John Wiley & Sons, New York (1999); Harlow and Lane, Antibodies: A Laboratory Manual (Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W.B. Saunders, Philadelphia, (1999)). A sample also can be processed to eliminate or minimize the presence of interfering substances. For example, a biological sample can be fractionated or purified to remove one or more materials that are not of interest. Methods of fractionating or purifying a biological sample include, but are not limited to, chromatographic methods such as liquid chromatography, ion-exchange chromatography, size-exclusion chromatography, or affinity chromatography. For use in the methods described herein, a sample can be in a variety of physical states. For example, a sample can be a liquid or solid, can be dissolved or suspended in a liquid, can be in an emulsion or gel, or can be absorbed onto a material.

Determining Expression Levels/Concentrations of Biomarkers

Gene expression can be detected as, e.g., protein or RNA expression of a target gene. That is, the presence or expression level (amount) of a gene can be determined by detecting and/or measuring the level of mRNA or protein expression of the gene. In some embodiments, gene expression can be detected as the activity of a protein encoded by a NF gene.

In one embodiment, the expression of a gene can be determined by detecting and/or measuring expression or concentration of a protein encoded by the gene. Methods of determining protein expression/concentration are well known in the art. A generally used method involves the use of antibodies specific for the target protein of interest. For example, methods of determining protein expression include, but are not limited to, western blot or dot blot analysis, immunohistochemistry (e.g., quantitative immunohistochemistry), immunocytochemistry, enzyme-linked immunosorbent assay (ELISA), enzyme-linked immunosorbent spot (ELISPOT; Coligan, J. E., et al., eds. (1995) Current Protocols in Immunology. Wiley, New York), radioimmunoassay, chemiluminescent immunoassay, electrochemiluminescence immunoassay, latex turbidimetric immunoassay, latex photometric immunoassay, immunochromatographic assay, and antibody array analysis (see, e.g., U.S. Publication Nos. 2003/0013208 and 2004/171068, the disclosures of each of which are incorporated herein by reference in their entirety). Further description of many of the methods above and additional methods for detecting protein expression can be found in, e.g., Sambrook et al. (supra).

In one example, the presence or amount of NF protein expression of a NF gene (e.g., NF-L) can be determined using a western blotting technique. For example, a lysate can be prepared from a biological sample, or the biological sample itself, can be contacted with Laemmli buffer and subjected to sodium-dodecyl sulfate polyacrylamide gel electrophoresis (SDS-PAGE). SDS-PAGE-resolved proteins, separated by size, can then be transferred to a filter membrane (e.g., nitrocellulose) and subjected to immunoblotting techniques using a detectably-labeled antibody specific to the protein of interest. The presence or amount of bound detectably-labeled antibody indicates the presence or amount of protein in the biological sample.

In one embodiment, the SimplePlex platform is used to measure the levels of NF-H (e.g., phosphorylated NF-H). SimplePlex is commercially available from Protein Simple (San Jose, CA, USA) (See Dysinger M, et al. J. Immunol. Methods. 451:1-10, 2017).

In one embodiment, an assay for measuring NF-L (e.g., phosphorylated NF-L) is employed. Assays for measuring NF-L in serum have been described (see, e.g., Gaiottino et al., PLoS ONE 8: e75091, 2013; Kuhle et al., J. Neurol. Neurosurg. Psychiatry 86(3): 273-279, 2014). In one example, blood serum from a subject is centrifuged at 1000 g for 10 minutes at room temperature and stored at –80° C. within 2 hours of collection. Serum NF-L concentrations can be measured (e.g., in duplicate) using ready-to-use enzyme linked immunosorbent assay (ELISA) (Mabtech AB, Nacka Strand, Sweden) or an electrochemiluminescence (ECL) immunoassay described in Gaiottino et al., PLoS ONE 8: e75091, 2013, or a single molecule array (SIMOA) method described in Disanto et al., Ann. Neurol. 81(6): 857-870, 2017. The assay methods have been compared in Kuhl et al., Clinical Chemistry and Laboratory Medicine 54 (10): 1655-1661, 2016. The SIMOA assay (particularly called the Simoa NF-light Advantage kit) is commercially available from Quanterix Corp. (Lexington, MA, USA).

In another example, an immunoassay can be used for detecting and/or measuring the protein expression of a gene (e.g., NF-H gene). As above, for the purposes of detection, an immunoassay can be performed with an antibody that bears a detection moiety (e.g., a fluorescent agent or enzyme). Proteins from a biological sample can be conjugated directly to a solid-phase matrix (e.g., a multi-well assay plate, nitrocellulose, agarose, sepharose, encoded particles, or magnetic beads) or it can be conjugated to a first member of a specific binding pair (e.g., biotin or streptavidin) that attaches to a solid-phase matrix upon binding to a second member of the specific binding pair (e.g., streptavidin or biotin). Such attachment to a solid-phase matrix allows the proteins to be purified away from other interfering or irrelevant components of the biological sample prior to contact with the detection antibody and also allows for subsequent washing of unbound antibody. Here, as above, the presence or amount of bound detectably-labeled antibody indicates the presence or amount of protein in the biological sample.

There is no particular restriction as to the form of the antibody and the present disclosure includes polyclonal antibodies, as well as monoclonal antibodies. The antiserum obtained by immunizing animals, such as rabbits with a protein or fragment thereof of the invention (i.e., a protein or an immunological fragment thereof of a NF protein), as well polyclonal and monoclonal antibodies of all classes, human antibodies, and humanized antibodies produced by genetic recombination, are also included.

An intact protein or its partial peptide may be used as the antigen for immunization. As partial peptides of the proteins, for example, the amino (N)-terminal fragment of the protein and the carboxy (C)-terminal fragment can be given.

A gene encoding a protein of interest or a fragment thereof (e.g., an immunological fragment) is inserted into a known expression vector, and, by transforming the host cells with the vector described herein, the desired protein or a fragment thereof is recovered from outside or inside the host cells using standard methods. This protein can be used as the sensitizing antigen. Also, cells expressing the protein, cell lysates, or a chemically synthesized protein of the invention may be also used as a sensitizing antigen.

The mammal that is immunized by the sensitizing antigen is not restricted; however, it is preferable to select animals by considering the compatibility with the parent cells used in cell fusion. Generally, animals belonging to the orders rodentia, lagomorpha, or primates are used. Examples of animals belonging to the order of rodentia that may be used include, for example, mice, rats, and hamsters. Examples of animals belonging to the order of lagomorpha that may be used include, for example, rabbits. Examples of animals belonging to the order of primates that may be used include, for example, monkeys. Examples of monkeys to be used include the infraorder catarrhini (old world monkeys), for example, *Macaca fascicularis*, rhesus monkeys, sacred baboons, and chimpanzees.

Well-known methods may be used to immunize animals with the sensitizing antigen. For example, the sensitizing antigen is injected intraperitoneally or subcutaneously into mammals. Specifically, the sensitizing antigen is suitably diluted and suspended in physiological saline, phosphate-buffered saline (PBS), and so on, and mixed with a suitable amount of general adjuvant if desired, for example, with Freund's complete adjuvant. Then, the solution is emulsified and injected into the mammal. Thereafter, the sensitizing antigen suitably mixed with Freund's incomplete adjuvant is preferably given several times every 4 to 21 days. A suitable carrier can also be used when immunizing and animal with the sensitizing antigen. After the immunization, the elevation in the level of serum antibody is detected by usual methods.

Polyclonal antibodies against the proteins of the present disclosure can be prepared as follows. After verifying that the desired serum antibody level has been reached, blood is withdrawn from the mammal sensitized with antigen. Serum is isolated from this blood using conventional methods. The serum containing the polyclonal antibody may be used as the polyclonal antibody, or according to needs, the polyclonal antibody-containing fraction may be further isolated from the serum. For example, a fraction of antibodies that specifically recognize the protein of the invention may be prepared by using an affinity column to which the protein is coupled. Then, the fraction may be further purified by using a Protein A or Protein G column in order to prepare immunoglobulin G or M.

To obtain monoclonal antibodies, after verifying that the desired serum antibody level has been reached in the mammal sensitized with the above-described antigen, immunocytes are taken from the mammal and used for cell fusion. For this purpose, splenocytes can be mentioned as preferable immunocytes. As parent cells fused with the above immunocytes, mammalian myeloma cells are preferably used. More preferably, myeloma cells that have acquired the feature, which can be used to distinguish fusion cells by agents, are used as the parent cell.

The cell fusion between the above immunocytes and myeloma cells can be conducted according to known methods, for example, the method by Milstein et al. (Galfre et al., *Methods Enzymol.* 73:3-46, 1981).

The hybridoma obtained from cell fusion is selected by culturing the cells in a standard selection medium, for example, HAT culture medium (medium containing hypoxanthine, aminopterin, and thymidine). The culture in this HAT medium is continued for a period sufficient enough for cells (non-fusion cells) other than the objective hybridoma to perish, usually from a few days to a few weeks. Then, the usual limiting dilution method is carried out, and the hybridoma producing the objective antibody is screened and cloned.

Other than the above method for obtaining hybridomas, by immunizing an animal other than humans with the antigen, a hybridoma producing the objective human antibodies having the activity to bind to proteins can be obtained by the method of sensitizing human lymphocytes, for example, human lymphocytes infected with the EB virus, with proteins, protein-expressing cells, or lysates thereof in vitro and fusing the sensitized lymphocytes with myeloma cells derived from human, for example, U266, having a permanent cell division ability.

The monoclonal antibodies obtained by transplanting the obtained hybridomas into the abdominal cavity of a mouse and extracting ascites can be purified by, for example, ammonium sulfate precipitation, protein A or protein G column, DEAE ion exchange chromatography, an affinity column to which the protein of the present disclosure is coupled, and so on.

Monoclonal antibodies can be also obtained as recombinant antibodies produced by using the genetic engineering technique (see, for example, Borrebaeck C. A. K. and Larrick, J. W., THERAPEUTIC MONOCLONAL ANTIBODIES, Published in the United Kingdom by MACMILLAN PUBLISHERS LTD (1990)). Recombinant antibodies are produced by cloning the encoding DNA from immunocytes, such as hybridoma or antibody-producing sensitized lymphocytes, incorporating into a suitable vector, and introducing this vector into a host to produce the antibody. The present disclosure encompasses such recombinant antibodies as well.

Antibodies or antibody fragments specific for a protein encoded by one or more biomarkers can also be generated by in vitro methods such as phage display.

Moreover, the antibody of the present disclosure may be an antibody fragment or modified-antibody, so long as it binds to a protein encoded by a biomarker of the invention. For instance, Fab, F (ab')2, Fv, or single chain Fv (scFv) in which the H chain Fv and the L chain Fv are suitably linked by a linker (Huston et al., *Proc. Natl. Acad. Sci. USA,* 85:5879-5883, (1988)) can be given as antibody fragments. Specifically, antibody fragments are generated by treating antibodies with enzymes, for example, papain or pepsin. Alternatively, they may be generated by constructing a gene encoding an antibody fragment, introducing this into an expression vector, and expressing this vector in suitable host cells (see, for example, Co et al., *J. Immunol.,* 152:2968-2976, 1994; Better et al., *Methods Enzymol.,* 178:476-496, 1989; Pluckthun et al., *Methods Enzymol.,* 178:497-515, 1989; Lamoyi, *Methods Enzymol.,* 121:652-663, 1986; Rousseaux et al., *Methods Enzymol.,* 121:663-669, 1986; Bird et al., *Trends Biotechnol.,* 9:132-137, 1991).

The antibodies may be conjugated to various molecules, such as fluorescent substances, radioactive substances, and luminescent substances. Methods to attach such moieties to an antibody are already established and conventional in the field (see, e.g., U.S. Pat. Nos. 5,057,313 and 5,156,840).

Examples of methods that assay the antigen-binding activity of the antibodies include, for example, measurement of absorbance, enzyme-linked immunosorbent assay (ELISA), enzyme immunoassay (EIA), radioimmunoassay (RIA), and/or immunofluorescence. For example, when using ELISA, a protein encoded by a biomarker of the invention is added to a plate coated with the antibodies of the present disclosure, and then, the antibody sample, for example, culture supernatants of antibody-producing cells, or purified antibodies are added. Then, secondary antibody recognizing the primary antibody, which is labeled by alkaline phosphatase and such enzymes, is added, the plate is incubated and washed, and the absorbance is measured to evaluate the antigen-binding activity after adding an enzyme substrate such as p-nitrophenyl phosphate. As the protein, a protein fragment, for example, a fragment comprising a C-terminus, or a fragment comprising an N-terminus may be used. To evaluate the activity of the antibody of the invention, BIAcore (Pharmacia) may be used.

By using these methods, the antibody of the invention and a sample presumed to contain a protein of the invention are contacted, and the protein encoded by a biomarker of the invention is detected or assayed by detecting or assaying the immune complex formed between the above-mentioned antibody and the protein.

Mass spectrometry based quantitation assay methods, for example, but not limited to, multiple reaction monitoring (MRM)-based approaches in combination with stable-isotope labeled internal standards, are an alternative to immunoassays for quantitative measurement of proteins. These approaches do not require the use of antibodies and so the analysis can be performed in a cost- and time-efficient manner (see, for example, Addona et al., *Nat. Biotechnol.,* 27:633-641, 2009; Kuzyk et al., *Mol. Cell Proteomics,* 8:1860-1877, 2009; Paulovich et al., *Proteomics Clin. Appl.,* 2:1386-1402, 2008). In addition, MRM offers superior multiplexing capabilities, allowing for the simultaneous quantification of numerous proteins in parallel. The basic theory of these methods has been well-established and widely utilized for drug metabolism and pharmacokinetics analysis of small molecules.

In another embodiment, the expression level of a NF gene of interest is determined by measuring RNA levels. A variety of suitable methods can be employed to detect and/or measure the level of mRNA expression of a gene. For example, mRNA expression can be determined using Northern blot or dot blot analysis, reverse transcriptase-PCR (RT-PCR; e.g., quantitative RT-PCR), in situ hybridization (e.g., quantitative in situ hybridization) or nucleic acid array (e.g., oligonucleotide arrays or gene chips) analysis. Details of such methods are described below and in, e.g., Sambrook et al., Molecular Cloning: A Laboratory Manual Second Edition vol. 1, 2 and 3. Cold Spring Harbor Laboratory Press: Cold Spring Harbor, New York, USA, November 1989; Gibson et al. (1999) *Genome Res.,* 6(10):995-1001; and Zhang et al. (2005) *Environ. Sci. Technol.,* 39(8):2777-2785; U.S. Publication No. 2004086915; European Patent No. 0543942; and U.S. Pat. No. 7,101,663; the disclosures of each of which are incorporated herein by reference in their entirety.

In one example, the presence or amount of one or more discrete mRNA populations in a biological sample can be determined by isolating total mRNA from the biological sample (see, e.g., Sambrook et al. (supra) and U.S. Pat. No. 6,812,341) and subjecting the isolated mRNA to agarose gel electrophoresis to separate the mRNA by size. The size-separated mRNAs are then transferred (e.g., by diffusion) to a solid support such as a nitrocellulose membrane. The presence or amount of one or more mRNA populations in the biological sample can then be determined using one or more detectably-labeled-polynucleotide probes, complementary to the mRNA sequence of interest, which bind to and thus render detectable their corresponding mRNA populations. Detectable-labels include, e.g., fluorescent (e.g., umbelliferone, fluorescein, fluorescein isothiocyanate, rhodamine, dichlorotriazinylamine fluorescein, dansyl chloride, allophycocyanin (APC), or phycoerythrin), luminescent (e.g., europium, terbium, Qdot™ nanoparticles supplied by the Quantum Dot Corporation, Palo Alto, CA), radiological (e.g., $^{125}$I, $^{131}$I, $^{35}$S, $^{32}$P, $^{33}$P or $^{3}$H), and enzymatic (horse-radish peroxidase, alkaline phosphatase, beta-galactosidase, or acetylcholinesterase) labels.

In another example, the presence or amount of discrete populations of mRNA (e.g., mRNA encoded by one or more NF genes) in a biological sample can be determined using nucleic acid (or oligonucleotide) arrays. For example, isolated mRNA from a biological sample can be amplified using RT-PCR with, e.g., random hexamer or oligo(dT)-primer mediated first strand synthesis. The amplicons can be fragmented into shorter segments. The RT-PCR step can be used to detectably-label the amplicons, or, optionally, the amplicons can be detectably-labeled subsequent to the RT-PCR step. For example, the detectable-label can be enzymatically (e.g., by nick-translation or kinase such as T4 polynucleotide kinase) or chemically conjugated to the amplicons using any of a variety of suitable techniques (see, e.g., Sambrook et al., supra). The detectably-labeled-amplicons are then contacted with a plurality of polynucleotide probe sets, each set containing one or more of a polynucleotide (e.g., an oligonucleotide) probe specific for (and capable of binding to) a corresponding amplicon, and where the plurality contains many probe sets each corresponding to a different amplicon. Generally, the probe sets are bound to a solid support and the position of each probe set is predetermined on the solid support. The binding of a detectably-labeled amplicon to a corresponding probe of a probe set indicates the presence or amount of a target mRNA in the biological sample. Additional methods for detecting mRNA expression using nucleic acid arrays are described in, e.g., U.S. Pat. Nos. 5,445,934; 6,027,880; 6,057,100; 6,156,501; 6,261,776; and 6,576,424; the disclosures of each of which are incorporated herein by reference in their entirety.

Methods of detecting and/or for quantifying a detectable label depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Methods for detecting or measuring gene expression (e.g., protein or mRNA expression) can optionally be performed in formats that allow for rapid preparation, processing, and analysis of multiple samples. This can be, for example, in multi-welled assay plates (e.g., 96 wells or 386 wells) or arrays (e.g., nucleic acid chips or protein chips). Stock solutions for various reagents can be provided manually or robotically, and subsequent sample preparation (e.g., RT-PCR, labeling, or cell fixation), pipetting, diluting, mixing, distribution, washing, incubating (e.g., hybridization), sample readout, data collection (optical data) and/or analysis (computer aided image analysis) can be done robotically using commercially available analysis software, robotics, and detection instrumentation capable of detecting the signal generated from the assay. Examples of such detectors include, but are not limited to, spectrophotometers, luminometers, fluorimeters, and devices that measure radioisotope decay. Exemplary high-throughput cell-based assays (e.g., detecting the presence or level of a target protein in a cell) can utilize ArrayScan® VTI HCS Reader or KinetiScan® HCS Reader technology (Cellomics Inc., Pittsburgh, PA).

In some embodiments, the expression level of one NF gene, two NF genes, or three NF genes can be assessed and/or measured.

To aid in detecting the presence or level of expression of one or more of the NF genes, any part of the nucleic acid sequence of the genes can be used, e.g., as hybridization polynucleotide probes or primers (e.g., for amplification or reverse transcription). The probes and primers can be oligonucleotides of sufficient length to provide specific hybridization to an RNA, DNA, cDNA, or fragments thereof isolated from a biological sample. Depending on the specific application, varying hybridization conditions can be employed to achieve varying degrees of selectivity of a probe or primer towards target sequence. The primers and probes can be detectably-labeled with reagents that facilitate detection (e.g., fluorescent labels, chemical labels (see, e.g., U.S. Pat. Nos. 4,582,789 and 4,563,417), or modified bases).

Standard stringency conditions are described by Sambrook, et al. (supra) and Haymes, et al. Nucleic Acid Hybridization, A Practical Approach, IRL Press, Washington, D.C. (1985). In order for a nucleic acid molecule to serve as a primer or probe it need only be sufficiently complementary in sequence to be able to form a stable double-stranded structure under the particular hybridization conditions (e.g., solvent and salt concentrations) employed.

Hybridization can be used to assess homology between two nucleic acid sequences. A nucleic acid sequence described herein, or a fragment thereof, can be used as a hybridization probe according to standard hybridization techniques. The hybridization of a probe of interest (e.g., a probe containing a portion of a nucleotide sequence described herein or its complement) to DNA, RNA, cDNA, or fragments thereof from a test source is an indication of the presence of DNA or RNA corresponding to the probe in the test source. Hybridization conditions are known to those skilled in the art and can be found in Current Protocols in Molecular Biology, John Wiley & Sons, N.Y., 6.3.1-6.3.6, 1991. Moderate hybridization conditions are defined as hybridization in 2× sodium chloride/sodium citrate (SSC) at 30° C., followed by a wash in 1×SSC, 0.1% SDS at 50° C. Highly stringent conditions are defined as hybridization in 6×SSC at 45° C., followed by a wash in 0.2×SSC, 0.1% SDS at 65° C.

Primers can be used in in a variety of PCR-type methods. For example, polymerase chain reaction (PCR) techniques can be used to amplify specific sequences from DNA as well as RNA, including sequences from total genomic DNA or total cellular RNA. The PCR primers are designed to flank the region that one is interested in amplifying. Primers can be located near the 5' end, the 3' end or anywhere within the nucleotide sequence that is to be amplified. The amplicon length is dictated by the experimental goals. For qPCR, the target length is closer to 100 base pairs and for standard PCR, it is near 500 base pairs. Generally, sequence information from the ends of the region of interest or beyond is employed to design oligonucleotide primers that are identical or similar in sequence to opposite strands of the template to be amplified. PCR primers can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair.

In addition, the nucleic acid sequences or fragments thereof (e.g., oligonucleotide probes) can be used in nucleic acid arrays for detection and/or quantitation of gene expression.

Methods of Treatment

The methods disclosed herein enable the assessment of whether or not a subject receiving an immunomodulator (e.g., immunosuppressant) therapy is likely to develop PML. A subject that is determined to be likely to develop PML can undergo a thorough assessment for additional indicators of PML, such as a brain scan indicating lesions consistent with PML and/or detection of JC virus in a sample obtained from the human subject. A subject that is determined to be likely to develop PML can have immunomodulator (e.g., immunosuppressant) treatment discontinued or modified to a lower dose of the immunomodulator (e.g., immunosuppressant). Conversely, a subject that is not determined to be likely to develop PML can continue to receive the immunomodulator (e.g., immunosuppressant) therapy without modification.

Kits

This disclosure also provides kits. In certain embodiments, the kit can include an antibody or antibodies that can be used to detect one or more of the biomarkers disclosed herein or their concentration or expression levels. For example, the kit can include an antibody that specifically binds NF-L. The antibodies in the kit may be monoclonal or polyclonal and can be further conjugated with a detectable label. In some embodiments, the kit includes probes that can be used to identify or detect any of the biomarkers disclosed herein. In some embodiments, the kit includes any of the nucleic acid arrays. In some embodiments, the kit includes probes and antibodies that can be used to identify or detect any of the biomarkers disclosed herein or their expression or expression levels. The kits can, optionally, contain instructions for detecting and/or measuring the concentration of one or more proteins or the levels of mRNA in a biological sample.

The kits can optionally include, e.g., a control (e.g., a concentration standard for the protein being assessed) or control labeled-amplicon set containing known amounts of one or more amplicons recognized by nucleic acid probes of the array. In some instances, the control can be an insert (e.g., a paper insert or electronic medium such as a CD, DVD, or floppy disk) containing an expression level or expression level ranges of one or more proteins (e.g., NF-L) or RNAs predictive of likelihood to develop PML.

In some embodiments, the kits can include one or more reagents for processing a biological sample (e.g., calibration reagents, buffers, diluents, color reagents, reagents to stop a reaction). For example, a kit can include reagents for isolating a protein from a biological sample and/or reagents for detecting the presence and/or amount of a protein in a biological sample (e.g., an antibody that binds to the protein that is the subject of the detection assay and/or an antibody that binds the antibody that binds to the protein).

In certain embodiments, the kit includes at least one microplate (e.g., a 96 well plate; i.e., 12 strips of 8 wells). The microplate can be provided with its corresponding plate cover. The microplate can be polystyrene or of any other suitable material. The microplate can have the antibody that is used to identify the presence of a particular biomarker coated inside each well. The antibody may be conjugated to a detectable label. The kit may also include at least one adhesive strip.

In some embodiments, the kits can include a software package for analyzing the results of, e.g., expression profile or a microarray analysis.

The kits can also include one or more antibodies for detecting the protein expression of any of the genes described herein (e.g., NF-L). For example, a kit can include (or in some cases consist of) one or a plurality of antibodies capable of specifically binding to one or more proteins encoded by any of the genes described herein and optionally, instructions for detecting and/or measuring the concentration of one or more proteins and/or a detection antibody comprising a detectably-labeled antibody that is capable of binding to at least one antibody of the plurality. In some embodiments, the kits can include antibodies that recognize NF-H, NF-L, and/or NF-M. In some embodiments, the kits can include antibodies that recognize pNF-H.

In certain embodiments, the kit can also optionally include one or more unit doses of an immunomodulator (e.g., immunosuppressant).

The kits described herein can also, optionally, include instructions for administering an immunomodulator (e.g., immunosuppressant), where the concentration of neurofilament detected predicts that a subject being treated with the immunomodulator (e.g., immunosuppressant) will or will not develop PML.

The following examples are provided to better illustrate the claimed invention and are not to be interpreted as limiting the scope of the invention. To the extent that specific materials are mentioned, it is merely for purposes of illustration and is not intended to limit the invention. One skilled in the art can develop equivalent means or reactants without the exercise of inventive capacity and without departing from the scope of the invention.

EXAMPLES

Figure 2:
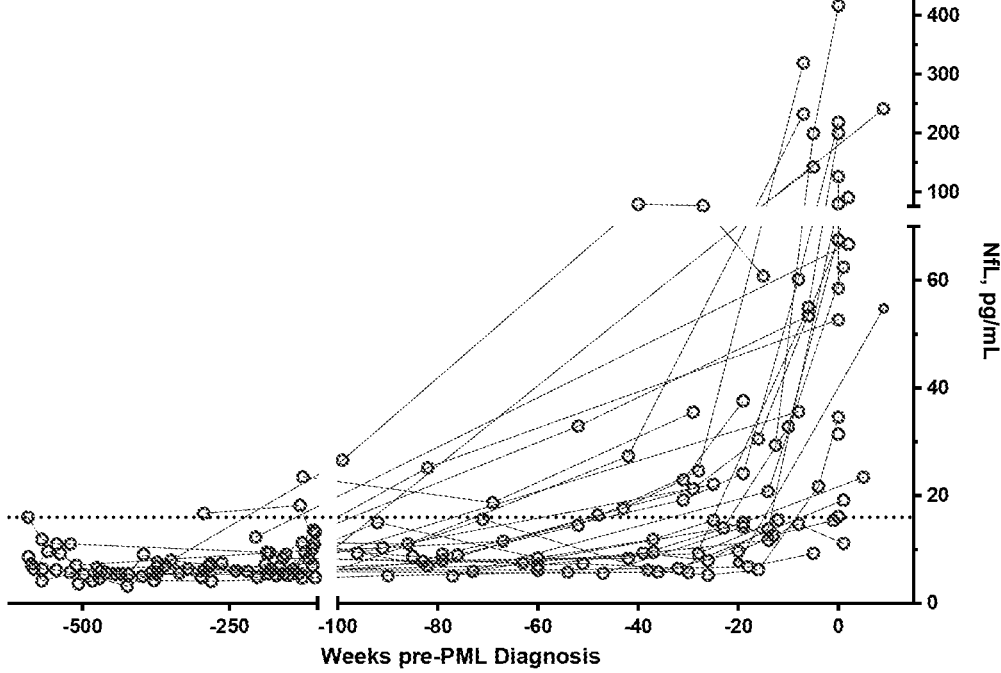
FIG. 2 is a graph depicting sNfL concentrations over time in natalizumab-treated PML patients.

Evaluation of Serum Neurofilament Light Chain as a Monitoring Biomarker for Natalizumab PML Longitudinal samples were analyzed from 38 natalizumab-treated PML patients and 106 natalizumab-treated non-PML patients (RESTORE/n=45, AFFIRM/n=61). 27 natalizumab-treated PML patients had informative timepoints, within 52 weeks from PML diagnosis. Serum neurofilament light chain (sNfL) concentrations were measured using SIMOA NF-Light® Advantage Kit, Quanterix.

sNfL levels were consistently low in natalizumab-treated non-PML patients (FIG. 1; RESTORE/n=45, median 7.1 pg/mL). Two patients with sNfL levels consistently >16 pg/mL were among oldest in the study (age 58 and 59 years).

sNfL concentrations were consistently low >2 years prior to PML diagnosis in patients that later developed PML (FIG. 2; median=7.8 pg/mL). Twenty out of 27 natalizumab-treated PML patients (74%) had increased sNfL 4-99 weeks prior to confirmed PML diagnosis (FIG. 2). The curve fitted to the group level data determined the inflection point of sNfL increase 20-25 weeks prior to PML diagnosis. Seven patients (26%) showed no increase in sNfL before PML diagnosis. Among those, two had no samples earlier than 20 weeks prior to PML, and one had consistently elevated sNfL concentrations at earlier timepoints. All tested natalizumab-treated PML patients had elevated sNfL concentrations at or post-PML diagnosis.

Figures 3, 4:
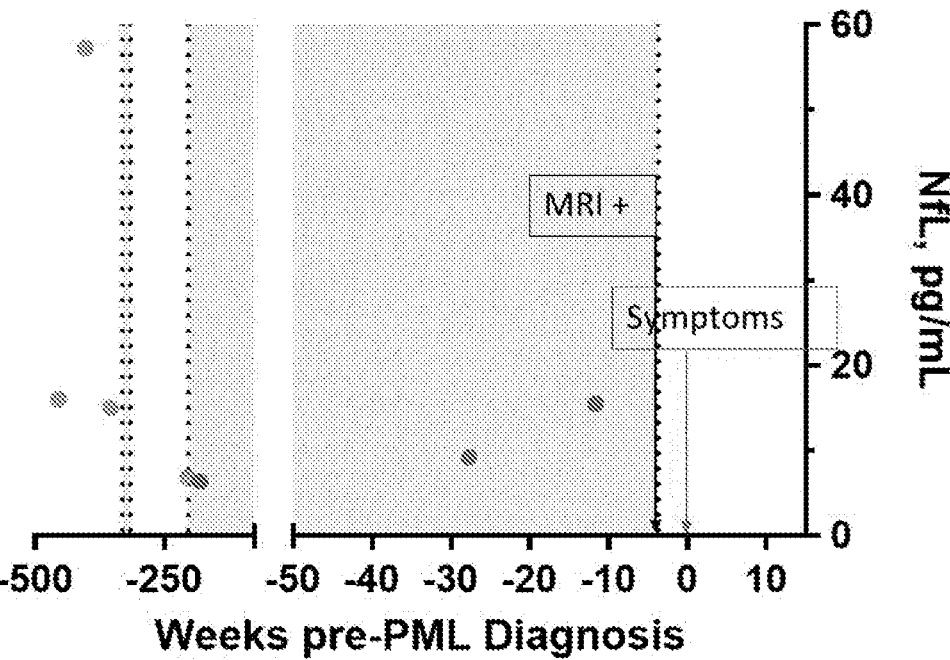
FIG. 3 is a temporal profile of sNfL concentrations over time in a natalizumab-treated patient who developed PML.
FIG. 4 is a temporal profile of sNfL concentrations over time in a natalizumab-treated patient who developed PML.
Figure 5:
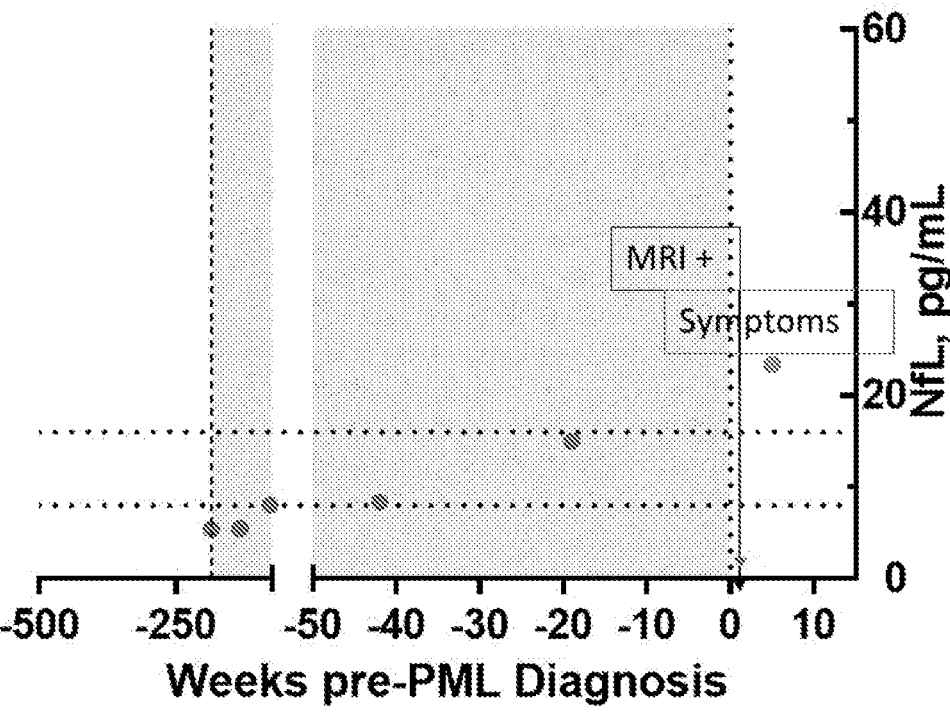
FIG. 5 is a temporal profile of sNfL concentrations over time in a natalizumab-treated patient who developed PML.

Temporal profiles were prepared of sNfL concentrations over time in natalizumab-treated patients who developed PML. At the time of PML diagnosis, the patients were asymptomatic and PML was detected by routine monitoring MRI (FIGS. 3, 4, and 5; grey shaded areas represent natalizumab infusions). sNFL levels were increased several weeks prior to PML detection by MRI.

Figure 6:
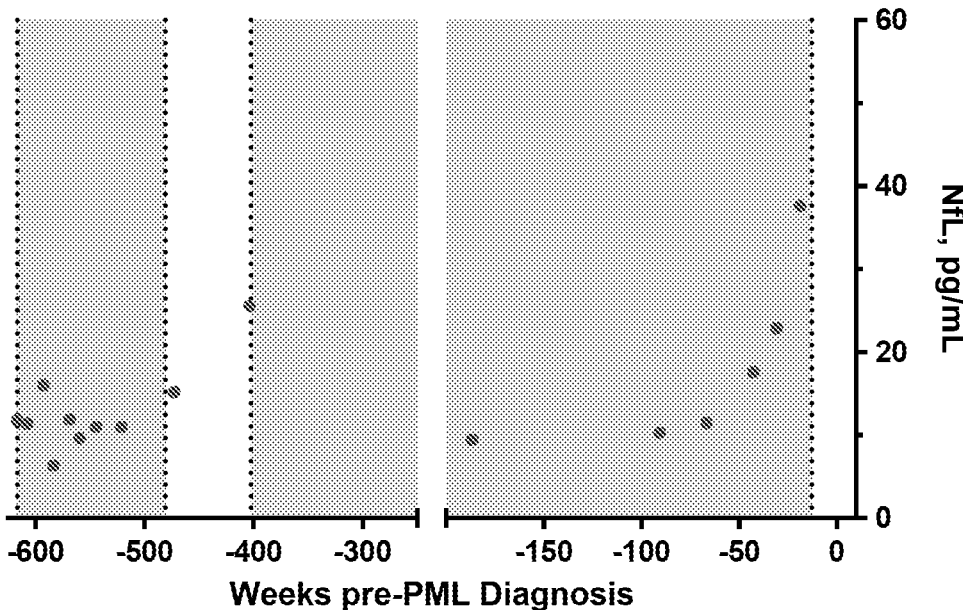
FIG. 6 is a temporal profile of sNfL concentrations over time in a natalizumab-treated patient who developed PML.

A temporal profile was prepared of sNfL concentration over time in a natalizumab-treated patient who developed PML (FIG. 6; grey shaded areas represent natalizumab infusions). At the time of PML diagnosis, the patient was symptomatic.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing the occurrence or severity of progressive multifocal leukoencephalopathy (PML) in a human subject with multiple sclerosis during natalizumab therapy, the method comprising:

administering multiple doses of natalizumab to a human subject over a period of at least six months;

measuring a first neurofilament level in a first biological sample obtained from the human subject at least six months after initiation of administration of the multiple doses;

measuring a second neurofilament level in a second biological sample obtained from the human subject after continued administration of natalizumab, wherein the second biological sample is obtained at least six months after the first biological sample is obtained, wherein, at the time the second biological sample is obtained, the human subject has not been diagnosed as having clinical symptoms of PML, and wherein the second neurofilament level is increased by at least 50% as compared to the first neurofilament level;

assessing the human subject for an indicator of PML selected from the group consisting of a brain scan indicating lesions consistent with PML, detection of John Cunningham (JC) virus in a sample obtained from the human subject, and a brain scan indicating lesions consistent with PML and detection of JC virus in a sample obtained from the human subject;

determining that the human subject has the indicator of PML and is likely to develop PML; and discontinuing natalizumab therapy or administering to the human subject a lower dose of natalizumab.

2. The method of claim 1, wherein JC virus is detected in a cerebrospinal fluid sample taken from the subject.

3. The method of claim 1, wherein, after measuring the second neurofilament level, the systemic level of natalizumab in the human subject is actively reduced by plasma exchange.

4. The method of claim 1, wherein, after measuring the second neurofilament level, the amount and/or frequency of natalizumab administered to the human subject is reduced as compared to the doses administered prior to measuring the second neurofilament level.

5. The method of claim 1, wherein, after measuring the second neurofilament level, treatment of the human subject with natalizumab is discontinued for a period of at least six months.

6. The method of claim 1, wherein, after measuring the second neurofilament level, treatment of the human subject with natalizumab is permanently discontinued.

7. The method of claim 1, wherein the human subject has received an organ, cell, or tissue transplant.

8. The method of claim 1, wherein the human subject has a cancer.

9. The method of claim 1, wherein the first and second biological samples are blood, serum, plasma, or cerebrospinal fluid.

* * * * *

SEQUENCE LISTING

```
<160> NUMBER OF SEQ ID NOS: 8

<210> SEQ ID NO 1
<211> LENGTH: 1026
<212> TYPE: PRT
<213> ORGANISM: Homo sapiens

<400> SEQUENCE: 1

Met Met Ser Phe Gly Gly Ala Asp Ala Leu Leu Gly Ala Pro Phe Ala
1               5                   10                  15

Pro Leu His Gly Gly Gly Ser Leu His Tyr Ala Leu Ala Arg Lys Gly
            20                  25                  30

Gly Ala Gly Gly Thr Arg Ser Ala Ala Gly Ser Ser Ser Gly Phe His
        35                  40                  45

Ser Trp Thr Arg Thr Ser Val Ser Ser Val Ser Ala Ser Pro Ser Arg
    50                  55                  60

Phe Arg Gly Ala Gly Ala Ala Ser Ser Thr Asp Ser Leu Asp Thr Leu
65                  70                  75                  80

Ser Asn Gly Pro Glu Gly Cys Met Val Ala Val Ala Thr Ser Arg Ser
                85                  90                  95

Glu Lys Glu Gln Leu Gln Ala Leu Asn Asp Arg Phe Ala Gly Tyr Ile
            100                 105                 110

Asp Lys Val Arg Gln Leu Glu Ala His Asn Arg Ser Leu Glu Gly Glu
        115                 120                 125

Ala Ala Ala Leu Arg Gln Gln Gln Ala Gly Arg Ser Ala Met Gly Glu
    130                 135                 140

Leu Tyr Glu Arg Glu Val Arg Glu Met Arg Gly Ala Val Leu Arg Leu
145                 150                 155                 160
```

-continued

```
Gly Ala Ala Arg Gly Gln Leu Arg Leu Glu Gln Glu His Leu Leu Glu
            165                 170                 175

Asp Ile Ala His Val Arg Gln Arg Leu Asp Asp Glu Ala Arg Gln Arg
            180                 185                 190

Glu Glu Ala Glu Ala Ala Ala Arg Ala Leu Ala Arg Phe Ala Gln Glu
            195                 200                 205

Ala Glu Ala Ala Arg Val Asp Leu Gln Lys Lys Ala Gln Ala Leu Gln
        210                 215                 220

Glu Glu Cys Gly Tyr Leu Arg Arg His His Gln Glu Glu Val Gly Glu
    225                 230                 235                 240

Leu Leu Gly Gln Ile Gln Gly Ser Gly Ala Ala Gln Ala Gln Met Gln
                245                 250                 255

Ala Glu Thr Arg Asp Ala Leu Lys Cys Asp Val Thr Ser Ala Leu Arg
            260                 265                 270

Glu Ile Arg Ala Gln Leu Glu Gly His Ala Val Gln Ser Thr Leu Gln
            275                 280                 285

Ser Glu Glu Trp Phe Arg Val Arg Leu Asp Arg Leu Ser Glu Ala Ala
        290                 295                 300

Lys Val Asn Thr Asp Ala Met Arg Ser Ala Gln Glu Glu Ile Thr Glu
    305                 310                 315                 320

Tyr Arg Arg Gln Leu Gln Ala Arg Thr Thr Glu Leu Glu Ala Leu Lys
                325                 330                 335

Ser Thr Lys Asp Ser Leu Glu Arg Gln Arg Ser Glu Leu Glu Asp Arg
            340                 345                 350

His Gln Ala Asp Ile Ala Ser Tyr Gln Glu Ala Ile Gln Gln Leu Asp
            355                 360                 365

Ala Glu Leu Arg Asn Thr Lys Trp Glu Met Ala Ala Gln Leu Arg Glu
        370                 375                 380

Tyr Gln Asp Leu Leu Asn Val Lys Met Ala Leu Asp Ile Glu Ile Ala
    385                 390                 395                 400

Ala Tyr Arg Lys Leu Leu Glu Gly Glu Glu Cys Arg Ile Gly Phe Gly
                405                 410                 415

Pro Ile Pro Phe Ser Leu Pro Glu Gly Leu Pro Lys Ile Pro Ser Val
            420                 425                 430

Ser Thr His Ile Lys Val Lys Ser Glu Glu Lys Ile Lys Val Val Glu
            435                 440                 445

Lys Ser Glu Lys Glu Thr Val Ile Val Glu Glu Gln Thr Glu Glu Thr
        450                 455                 460

Gln Val Thr Glu Glu Val Thr Glu Glu Glu Lys Glu Ala Lys Glu
    465                 470                 475                 480

Glu Glu Gly Lys Glu Glu Glu Gly Gly Glu Glu Glu Ala Glu Gly
                485                 490                 495

Gly Glu Glu Glu Thr Lys Ser Pro Pro Ala Glu Glu Ala Ala Ser Pro
            500                 505                 510

Glu Lys Glu Ala Lys Ser Pro Val Lys Glu Glu Ala Lys Ser Pro Ala
            515                 520                 525

Glu Ala Lys Ser Pro Glu Lys Glu Glu Ala Lys Ser Pro Ala Glu Val
        530                 535                 540

Lys Ser Pro Glu Lys Ala Lys Ser Pro Ala Lys Glu Glu Ala Lys Ser
    545                 550                 555                 560

Pro Pro Glu Ala Lys Ser Pro Glu Lys Glu Glu Ala Lys Ser Pro Ala
                565                 570                 575
```

-continued

```
Glu Val Lys Ser Pro Glu Lys Ala Lys Ser Pro Ala Lys Glu Glu Ala
            580                 585                 590

Lys Ser Pro Ala Glu Ala Lys Ser Pro Glu Lys Ala Lys Ser Pro Val
            595                 600                 605

Lys Glu Glu Ala Lys Ser Pro Ala Glu Ala Lys Ser Pro Val Lys Glu
            610                 615                 620

Glu Ala Lys Ser Pro Ala Glu Val Lys Ser Pro Glu Lys Ala Lys Ser
625                 630                 635                 640

Pro Thr Lys Glu Glu Ala Lys Ser Pro Glu Lys Ala Lys Ser Pro Glu
                645                 650                 655

Lys Ala Lys Ser Pro Glu Lys Glu Glu Ala Lys Ser Pro Glu Lys Ala
                660                 665                 670

Lys Ser Pro Val Lys Ala Glu Ala Lys Ser Pro Glu Lys Ala Lys Ser
                675                 680                 685

Pro Val Lys Ala Glu Ala Lys Ser Pro Glu Lys Ala Lys Ser Pro Val
                690                 695                 700

Lys Glu Glu Ala Lys Ser Pro Glu Lys Ala Lys Ser Pro Val Lys Glu
705                 710                 715                 720

Glu Ala Lys Ser Pro Glu Lys Ala Lys Ser Pro Val Lys Glu Glu Ala
                725                 730                 735

Lys Thr Pro Glu Lys Ala Lys Ser Pro Val Lys Glu Glu Ala Lys Ser
                740                 745                 750

Pro Glu Lys Ala Lys Ser Pro Glu Lys Ala Lys Thr Leu Asp Val Lys
                755                 760                 765

Ser Pro Glu Ala Lys Thr Pro Ala Lys Glu Glu Ala Arg Ser Pro Ala
                770                 775                 780

Asp Lys Phe Pro Glu Lys Ala Lys Ser Pro Val Lys Glu Glu Val Lys
785                 790                 795                 800

Ser Pro Glu Lys Ala Lys Ser Pro Leu Lys Glu Asp Ala Lys Ala Pro
                805                 810                 815

Glu Lys Glu Ile Pro Lys Lys Glu Glu Val Lys Ser Pro Val Lys Glu
                820                 825                 830

Glu Glu Lys Pro Gln Glu Val Lys Val Lys Glu Pro Pro Lys Lys Ala
                835                 840                 845

Glu Glu Glu Lys Ala Pro Ala Thr Pro Lys Thr Glu Glu Lys Lys Asp
                850                 855                 860

Ser Lys Lys Glu Glu Ala Pro Lys Lys Glu Ala Pro Lys Pro Lys Val
865                 870                 875                 880

Glu Glu Lys Lys Glu Pro Ala Val Glu Lys Pro Lys Glu Ser Lys Val
                885                 890                 895

Glu Ala Lys Lys Glu Glu Ala Glu Asp Lys Lys Lys Val Pro Thr Pro
                900                 905                 910

Glu Lys Glu Ala Pro Ala Lys Val Glu Val Lys Glu Asp Ala Lys Pro
                915                 920                 925

Lys Glu Lys Thr Glu Val Ala Lys Lys Glu Pro Asp Asp Ala Lys Ala
            930                 935                 940

Lys Glu Pro Ser Lys Pro Ala Glu Lys Lys Glu Ala Ala Pro Glu Lys
945                 950                 955                 960

Lys Asp Thr Lys Glu Glu Lys Ala Lys Lys Pro Glu Glu Lys Pro Lys
                965                 970                 975

Thr Glu Ala Lys Ala Lys Glu Asp Asp Lys Thr Leu Ser Lys Glu Pro
                980                 985                 990
```

-continued

```
Ser Lys Pro Lys Ala Glu Lys Ala  Glu Lys Ser Ser Ser  Thr Asp Gln
        995                  1000                 1005

Lys Asp  Ser Lys Pro Pro Glu  Lys Ala Thr Glu Asp  Lys Ala Ala
    1010                 1015                 1020

Lys Gly  Lys
    1025

<210> SEQ ID NO 2
<211> LENGTH: 543
<212> TYPE: PRT
<213> ORGANISM: Homo sapiens

<400> SEQUENCE: 2

Met Ser Ser Phe Ser Tyr Glu Pro Tyr Tyr Ser Thr Ser Tyr Lys Arg
1               5                   10                  15

Arg Tyr Val Glu Thr Pro Arg Val His Ile Ser Ser Val Arg Ser Gly
            20                  25                  30

Tyr Ser Thr Ala Arg Ser Ala Tyr Ser Ser Tyr Ser Ala Pro Val Ser
            35                  40                  45

Ser Ser Leu Ser Val Arg Arg Ser Tyr Ser Ser Ser Ser Gly Ser Leu
    50                  55                  60

Met Pro Ser Leu Glu Asn Leu Asp Leu Ser Gln Val Ala Ala Ile Ser
65                  70                  75                  80

Asn Asp Leu Lys Ser Ile Arg Thr Gln Glu Lys Ala Gln Leu Gln Asp
                85                  90                  95

Leu Asn Asp Arg Phe Ala Ser Phe Ile Glu Arg Val His Glu Leu Glu
            100                 105                 110

Gln Gln Asn Lys Val Leu Glu Ala Glu Leu Leu Val Leu Arg Gln Lys
            115                 120                 125

His Ser Glu Pro Ser Arg Phe Arg Ala Leu Tyr Glu Gln Glu Ile Arg
    130                 135                 140

Asp Leu Arg Leu Ala Ala Glu Asp Ala Thr Asn Glu Lys Gln Ala Leu
145                 150                 155                 160

Gln Gly Glu Arg Glu Gly Leu Glu Glu Thr Leu Arg Asn Leu Gln Ala
                165                 170                 175

Arg Tyr Glu Glu Glu Val Leu Ser Arg Glu Asp Ala Glu Gly Arg Leu
            180                 185                 190

Met Glu Ala Arg Lys Gly Ala Asp Glu Ala Ala Leu Ala Arg Ala Glu
            195                 200                 205

Leu Glu Lys Arg Ile Asp Ser Leu Met Asp Glu Ile Ser Phe Leu Lys
    210                 215                 220

Lys Val His Glu Glu Glu Ile Ala Glu Leu Gln Ala Gln Ile Gln Tyr
225                 230                 235                 240

Ala Gln Ile Ser Val Glu Met Asp Val Thr Lys Pro Asp Leu Ser Ala
                245                 250                 255

Ala Leu Lys Asp Ile Arg Ala Gln Tyr Glu Lys Leu Ala Ala Lys Asn
            260                 265                 270

Met Gln Asn Ala Glu Glu Trp Phe Lys Ser Arg Phe Thr Val Leu Thr
            275                 280                 285

Glu Ser Ala Ala Lys Asn Thr Asp Ala Val Arg Ala Ala Lys Asp Glu
    290                 295                 300

Val Ser Glu Ser Arg Arg Leu Leu Lys Ala Lys Thr Leu Glu Ile Glu
305                 310                 315                 320

Ala Cys Arg Gly Met Asn Glu Ala Leu Glu Lys Gln Leu Gln Glu Leu
                325                 330                 335
```

```
Glu Asp Lys Gln Asn Ala Asp Ile Ser Ala Met Gln Asp Thr Ile Asn
            340                 345                 350

Lys Leu Glu Asn Glu Leu Arg Thr Thr Lys Ser Glu Met Ala Arg Tyr
            355                 360                 365

Leu Lys Glu Tyr Gln Asp Leu Leu Asn Val Lys Met Ala Leu Asp Ile
            370                 375                 380

Glu Ile Ala Ala Tyr Arg Lys Leu Leu Glu Gly Glu Glu Thr Arg Leu
385                 390                 395                 400

Ser Phe Thr Ser Val Gly Ser Ile Thr Ser Gly Tyr Ser Gln Ser Ser
                405                 410                 415

Gln Val Phe Gly Arg Ser Ala Tyr Gly Gly Leu Gln Thr Ser Ser Tyr
            420                 425                 430

Leu Met Ser Thr Arg Ser Phe Pro Ser Tyr Tyr Thr Ser His Val Gln
            435                 440                 445

Glu Glu Gln Ile Glu Val Glu Glu Thr Ile Glu Ala Ala Lys Ala Glu
            450                 455                 460

Glu Ala Lys Asp Glu Pro Pro Ser Glu Gly Glu Ala Glu Glu Glu Glu
465                 470                 475                 480

Lys Asp Lys Glu Glu Ala Glu Glu Glu Glu Ala Ala Glu Glu Glu Glu
                485                 490                 495

Ala Ala Lys Glu Glu Ser Glu Glu Ala Lys Glu Glu Glu Glu Gly Gly
            500                 505                 510

Glu Gly Glu Glu Gly Glu Glu Thr Lys Glu Ala Glu Glu Glu Glu Lys
            515                 520                 525

Lys Val Glu Gly Ala Gly Glu Glu Gln Ala Ala Lys Lys Lys Asp
    530                 535                 540

<210> SEQ ID NO 3
<211> LENGTH: 916
<212> TYPE: PRT
<213> ORGANISM: Homo sapiens

<400> SEQUENCE: 3

Met Ser Tyr Thr Leu Asp Ser Leu Gly Asn Pro Ser Ala Tyr Arg Arg
1               5                   10                  15

Val Thr Glu Thr Arg Ser Ser Phe Ser Arg Val Ser Gly Ser Pro Ser
                20                  25                  30

Ser Gly Phe Arg Ser Gln Ser Trp Ser Arg Gly Ser Pro Ser Thr Val
            35                  40                  45

Ser Ser Ser Tyr Lys Arg Ser Met Leu Ala Pro Arg Leu Ala Tyr Ser
    50                  55                  60

Ser Ala Met Leu Ser Ser Ala Glu Ser Ser Leu Asp Phe Ser Gln Ser
65                  70                  75                  80

Ser Ser Leu Leu Asn Gly Gly Ser Gly Pro Gly Gly Asp Tyr Lys Leu
                85                  90                  95

Ser Arg Ser Asn Glu Lys Glu Gln Leu Gln Gly Leu Asn Asp Arg Phe
            100                 105                 110

Ala Gly Tyr Ile Glu Lys Val His Tyr Leu Glu Gln Gln Asn Lys Glu
            115                 120                 125

Ile Glu Ala Glu Ile Gln Ala Leu Arg Gln Lys Gln Ala Ser His Ala
    130                 135                 140

Gln Leu Gly Asp Ala Tyr Asp Gln Glu Ile Arg Glu Leu Arg Ala Thr
145                 150                 155                 160
```

```
Leu Glu Met Val Asn His Glu Lys Ala Gln Val Gln Leu Asp Ser Asp
            165                 170                 175

His Leu Glu Glu Asp Ile His Arg Leu Lys Glu Arg Phe Glu Glu Glu
            180                 185                 190

Ala Arg Leu Arg Asp Asp Thr Glu Ala Ala Ile Arg Ala Leu Arg Lys
            195                 200                 205

Asp Ile Glu Glu Ala Ser Leu Val Lys Val Glu Leu Asp Lys Lys Val
    210                 215                 220

Gln Ser Leu Gln Asp Glu Val Ala Phe Leu Arg Ser Asn His Glu Glu
225                 230                 235                 240

Glu Val Ala Asp Leu Leu Ala Gln Ile Gln Ala Ser His Ile Thr Val
            245                 250                 255

Glu Arg Lys Asp Tyr Leu Lys Thr Asp Ile Ser Thr Ala Leu Lys Glu
            260                 265                 270

Ile Arg Ser Gln Leu Glu Ser His Ser Asp Gln Asn Met His Gln Ala
            275                 280                 285

Glu Glu Trp Phe Lys Cys Arg Tyr Ala Lys Leu Thr Glu Ala Ala Glu
            290                 295                 300

Gln Asn Lys Glu Ala Ile Arg Ser Ala Lys Glu Glu Ile Ala Glu Tyr
305                 310                 315                 320

Arg Arg Gln Leu Gln Ser Lys Ser Ile Glu Leu Glu Ser Val Arg Gly
            325                 330                 335

Thr Lys Glu Ser Leu Glu Arg Gln Leu Ser Asp Ile Glu Glu Arg His
            340                 345                 350

Asn His Asp Leu Ser Ser Tyr Gln Asp Thr Ile Gln Gln Leu Glu Asn
            355                 360                 365

Glu Leu Arg Gly Thr Lys Trp Glu Met Ala Arg His Leu Arg Glu Tyr
            370                 375                 380

Gln Asp Leu Leu Asn Val Lys Met Ala Leu Asp Ile Glu Ile Ala Ala
385                 390                 395                 400

Tyr Arg Lys Leu Leu Glu Gly Glu Glu Thr Arg Phe Ser Thr Phe Ala
            405                 410                 415

Gly Ser Ile Thr Gly Pro Leu Tyr Thr His Arg Pro Pro Ile Thr Ile
            420                 425                 430

Ser Ser Lys Ile Gln Lys Pro Lys Val Glu Ala Pro Lys Leu Lys Val
            435                 440                 445

Gln His Lys Phe Val Glu Glu Ile Ile Glu Glu Thr Lys Val Glu Asp
    450                 455                 460

Glu Lys Ser Glu Met Glu Glu Ala Leu Thr Ala Ile Thr Glu Glu Leu
465                 470                 475                 480

Ala Val Ser Met Lys Glu Glu Lys Lys Glu Ala Ala Glu Glu Lys Glu
            485                 490                 495

Glu Glu Pro Glu Ala Glu Glu Glu Val Ala Ala Lys Lys Ser Pro
            500                 505                 510

Val Lys Ala Thr Ala Pro Glu Val Lys Glu Glu Glu Gly Glu Lys Glu
            515                 520                 525

Glu Glu Glu Gly Gln Glu Glu Glu Glu Glu Asp Glu Gly Ala Lys
            530                 535                 540

Ser Asp Gln Ala Glu Glu Gly Gly Ser Glu Lys Glu Gly Ser Ser Glu
545                 550                 555                 560

Lys Glu Glu Gly Glu Gln Glu Glu Gly Glu Thr Glu Ala Glu Ala Glu
            565                 570                 575
```

-continued

```
Gly Glu Glu Ala Glu Ala Lys Glu Glu Lys Lys Val Glu Glu Lys Ser
            580                 585                 590

Glu Glu Val Ala Thr Lys Glu Glu Leu Val Ala Asp Ala Lys Val Glu
            595                 600                 605

Lys Pro Glu Lys Ala Lys Ser Pro Val Pro Lys Ser Pro Val Glu Glu
        610                 615                 620

Lys Gly Lys Ser Pro Val Pro Lys Ser Pro Val Glu Glu Lys Gly Lys
625                 630                 635                 640

Ser Pro Val Pro Lys Ser Pro Val Glu Glu Lys Gly Lys Ser Pro Val
                645                 650                 655

Pro Lys Ser Pro Val Glu Glu Lys Gly Lys Ser Pro Val Ser Lys Ser
            660                 665                 670

Pro Val Glu Glu Lys Ala Lys Ser Pro Val Pro Lys Ser Pro Val Glu
            675                 680                 685

Glu Ala Lys Ser Lys Ala Glu Val Gly Lys Gly Glu Gln Lys Glu Glu
        690                 695                 700

Glu Glu Lys Glu Val Lys Glu Ala Pro Lys Glu Glu Lys Val Glu Lys
705                 710                 715                 720

Lys Glu Glu Lys Pro Lys Asp Val Pro Glu Lys Lys Lys Ala Glu Ser
                725                 730                 735

Pro Val Lys Glu Glu Ala Val Ala Glu Val Val Thr Ile Thr Lys Ser
            740                 745                 750

Val Lys Val His Leu Glu Lys Glu Thr Lys Glu Glu Gly Lys Pro Leu
            755                 760                 765

Gln Gln Glu Lys Glu Lys Glu Lys Ala Gly Gly Glu Gly Gly Ser Glu
        770                 775                 780

Glu Glu Gly Ser Asp Lys Gly Ala Lys Gly Ser Arg Lys Glu Asp Ile
785                 790                 795                 800

Ala Val Asn Gly Glu Val Glu Gly Lys Glu Glu Val Glu Gln Glu Thr
                805                 810                 815

Lys Glu Lys Gly Ser Gly Arg Glu Glu Glu Lys Gly Val Val Thr Asn
            820                 825                 830

Gly Leu Asp Leu Ser Pro Ala Asp Glu Lys Lys Gly Gly Asp Lys Ser
            835                 840                 845

Glu Glu Lys Val Val Val Thr Lys Thr Val Glu Lys Ile Thr Ser Glu
        850                 855                 860

Gly Gly Asp Gly Ala Thr Lys Tyr Ile Thr Lys Ser Val Thr Val Thr
865                 870                 875                 880

Gln Lys Val Glu Glu His Glu Glu Thr Phe Glu Glu Lys Leu Val Ser
                885                 890                 895

Thr Lys Lys Val Glu Lys Val Thr Ser His Ala Ile Val Lys Glu Val
            900                 905                 910

Thr Gln Ser Asp
        915
```

<210> SEQ ID NO 4

<400> SEQUENCE: 4

000

<210> SEQ ID NO 5
<211> LENGTH: 1020
<212> TYPE: PRT
<213> ORGANISM: Homo sapiens -continued

<400> SEQUENCE: 5

```
Met Met Ser Phe Gly Gly Ala Asp Ala Leu Leu Gly Ala Pro Phe Ala
1               5                   10                  15

Pro Leu His Gly Gly Gly Ser Leu His Tyr Ala Leu Ala Arg Lys Gly
                20                  25                  30

Gly Ala Gly Gly Thr Arg Ser Ala Ala Gly Ser Ser Ser Gly Phe His
            35                  40                  45

Ser Trp Thr Arg Thr Ser Val Ser Ser Val Ser Ala Ser Pro Ser Arg
    50                  55                  60

Phe Arg Gly Ala Gly Ala Ala Ser Ser Thr Asp Ser Leu Asp Thr Leu
65                  70                  75                  80

Ser Asn Gly Pro Glu Gly Cys Met Val Ala Val Ala Thr Ser Arg Ser
                85                  90                  95

Glu Lys Glu Gln Leu Gln Ala Leu Asn Asp Arg Phe Ala Gly Tyr Ile
            100                 105                 110

Asp Lys Val Arg Gln Leu Glu Ala His Asn Arg Ser Leu Glu Gly Glu
            115                 120                 125

Ala Ala Ala Leu Arg Gln Gln Ala Gly Arg Ser Ala Met Gly Glu
        130                 135                 140

Leu Tyr Glu Arg Glu Val Arg Glu Met Arg Gly Ala Val Leu Arg Leu
145                 150                 155                 160

Gly Ala Ala Arg Gly Gln Leu Arg Leu Glu Gln Glu His Leu Leu Glu
                165                 170                 175

Asp Ile Ala His Val Arg Gln Arg Leu Asp Asp Glu Ala Arg Gln Arg
            180                 185                 190

Glu Glu Ala Glu Ala Ala Ala Arg Ala Leu Ala Arg Phe Ala Gln Glu
            195                 200                 205

Ala Glu Ala Ala Arg Val Asp Leu Gln Lys Lys Ala Gln Ala Leu Gln
        210                 215                 220

Glu Glu Cys Gly Tyr Leu Arg Arg His His Gln Glu Glu Val Gly Glu
225                 230                 235                 240

Leu Leu Gly Gln Ile Gln Gly Ser Gly Ala Ala Gln Ala Gln Met Gln
                245                 250                 255

Ala Glu Thr Arg Asp Ala Leu Lys Cys Asp Val Thr Ser Ala Leu Arg
            260                 265                 270

Glu Ile Arg Ala Gln Leu Glu Gly His Ala Val Gln Ser Thr Leu Gln
            275                 280                 285

Ser Glu Glu Trp Phe Arg Val Arg Leu Asp Arg Leu Ser Glu Ala Ala
    290                 295                 300

Lys Val Asn Thr Asp Ala Met Arg Ser Ala Gln Glu Glu Ile Thr Glu
305                 310                 315                 320

Tyr Arg Arg Gln Leu Gln Ala Arg Thr Thr Glu Leu Glu Ala Leu Lys
                325                 330                 335

Ser Thr Lys Asp Ser Leu Glu Arg Gln Arg Ser Glu Leu Glu Asp Arg
            340                 345                 350

His Gln Ala Asp Ile Ala Ser Tyr Gln Glu Ala Ile Gln Gln Leu Asp
            355                 360                 365

Ala Glu Leu Arg Asn Thr Lys Trp Glu Met Ala Ala Gln Leu Arg Glu
        370                 375                 380

Tyr Gln Asp Leu Leu Asn Val Lys Met Ala Leu Asp Ile Glu Ile Ala
385                 390                 395                 400

Ala Tyr Arg Lys Leu Leu Glu Gly Glu Glu Cys Arg Ile Gly Phe Gly
                405                 410                 415
```

-continued

```
Pro Ile Pro Phe Ser Leu Pro Glu Gly Leu Pro Lys Ile Pro Ser Val
        420                 425                 430

Ser Thr His Ile Lys Val Lys Ser Glu Glu Lys Ile Lys Val Val Glu
        435                 440                 445

Lys Ser Glu Lys Glu Thr Val Ile Val Glu Glu Gln Thr Glu Glu Thr
        450                 455                 460

Gln Val Thr Glu Glu Val Thr Glu Glu Glu Lys Glu Ala Lys Glu
465                 470                 475                 480

Glu Glu Gly Lys Glu Glu Gly Gly Glu Glu Glu Ala Glu Gly
                485                 490                 495

Gly Glu Glu Glu Thr Lys Ser Pro Pro Ala Glu Glu Ala Ala Ser Pro
        500                 505                 510

Glu Lys Glu Ala Lys Ser Pro Val Lys Glu Glu Ala Lys Ser Pro Ala
        515                 520                 525

Glu Ala Lys Ser Pro Glu Lys Glu Glu Ala Lys Ser Pro Ala Glu Val
        530                 535                 540

Lys Ser Pro Glu Lys Ala Lys Ser Pro Ala Lys Glu Glu Ala Lys Ser
545                 550                 555                 560

Pro Pro Glu Ala Lys Ser Pro Glu Lys Glu Glu Ala Lys Ser Pro Ala
                565                 570                 575

Glu Val Lys Ser Pro Glu Lys Ala Lys Ser Pro Ala Lys Glu Glu Ala
                580                 585                 590

Lys Ser Pro Ala Glu Ala Lys Ser Pro Glu Lys Ala Lys Ser Pro Val
        595                 600                 605

Lys Glu Glu Ala Lys Ser Pro Ala Glu Ala Lys Ser Pro Val Lys Glu
        610                 615                 620

Glu Ala Lys Ser Pro Ala Glu Val Lys Ser Pro Glu Lys Ala Lys Ser
625                 630                 635                 640

Pro Thr Lys Glu Glu Ala Lys Ser Pro Glu Lys Ala Lys Ser Pro Glu
                645                 650                 655

Lys Glu Glu Ala Lys Ser Pro Glu Lys Ala Lys Ser Pro Val Lys Ala
                660                 665                 670

Glu Ala Lys Ser Pro Glu Lys Ala Lys Ser Pro Val Lys Ala Glu Ala
        675                 680                 685

Lys Ser Pro Glu Lys Ala Lys Ser Pro Val Lys Glu Glu Ala Lys Ser
        690                 695                 700

Pro Glu Lys Ala Lys Ser Pro Val Lys Glu Glu Ala Lys Ser Pro Glu
705                 710                 715                 720

Lys Ala Lys Ser Pro Val Lys Glu Glu Ala Lys Thr Pro Glu Lys Ala
                725                 730                 735

Lys Ser Pro Val Lys Glu Glu Ala Lys Ser Pro Glu Lys Ala Lys Ser
        740                 745                 750

Pro Glu Lys Ala Lys Thr Leu Asp Val Lys Ser Pro Glu Ala Lys Thr
        755                 760                 765

Pro Ala Lys Glu Glu Ala Arg Ser Pro Ala Asp Lys Phe Pro Glu Lys
        770                 775                 780

Ala Lys Ser Pro Val Lys Glu Glu Val Lys Ser Pro Glu Lys Ala Lys
785                 790                 795                 800

Ser Pro Leu Lys Glu Asp Ala Lys Ala Pro Glu Lys Glu Ile Pro Lys
                805                 810                 815

Lys Glu Glu Val Lys Ser Pro Val Lys Glu Glu Glu Lys Pro Gln Glu
        820                 825                 830
```

-continued

```
Val Lys Val Lys Glu Pro Pro Lys Lys Ala Glu Glu Glu Lys Ala Pro
        835                 840                 845

Ala Thr Pro Lys Thr Glu Glu Lys Lys Asp Ser Lys Lys Glu Glu Ala
    850                 855                 860

Pro Lys Lys Glu Ala Pro Lys Pro Lys Val Glu Glu Lys Lys Glu Pro
865                 870                 875                 880

Ala Val Glu Lys Pro Lys Glu Ser Lys Val Glu Ala Lys Lys Glu Glu
                885                 890                 895

Ala Glu Asp Lys Lys Lys Val Pro Thr Pro Glu Lys Glu Ala Pro Ala
            900                 905                 910

Lys Val Glu Val Lys Glu Asp Ala Lys Pro Lys Glu Lys Thr Glu Val
        915                 920                 925

Ala Lys Lys Glu Pro Asp Asp Ala Lys Ala Lys Glu Pro Ser Lys Pro
    930                 935                 940

Ala Glu Lys Lys Glu Ala Ala Pro Glu Lys Lys Asp Thr Lys Glu Glu
945                 950                 955                 960

Lys Ala Lys Lys Pro Glu Glu Lys Pro Lys Thr Glu Ala Lys Ala Lys
                965                 970                 975

Glu Asp Asp Lys Thr Leu Ser Lys Glu Pro Ser Lys Pro Lys Ala Glu
            980                 985                 990

Lys Ala Glu Lys Ser Ser Ser Thr  Asp Gln Lys Asp Ser  Lys Pro Pro
        995                 1000                1005

Glu Lys  Ala Thr Glu Asp Lys  Ala Ala Lys Gly Lys
    1010                1015                1020
```

<210> SEQ ID NO 6
<211> LENGTH: 540
<212> TYPE: PRT
<213> ORGANISM: Homo sapiens

<400> SEQUENCE: 6

```
Met Ala Arg His Leu Arg Glu Tyr Gln Asp Leu Leu Asn Val Lys Met
1               5                   10                  15

Ala Leu Asp Ile Glu Ile Ala Ala Tyr Arg Lys Leu Leu Glu Gly Glu
            20                  25                  30

Glu Thr Arg Phe Ser Thr Phe Ala Gly Ser Ile Thr Gly Pro Leu Tyr
        35                  40                  45

Thr His Arg Pro Pro Ile Thr Ile Ser Ser Lys Ile Gln Lys Pro Lys
    50                  55                  60

Val Glu Ala Pro Lys Leu Lys Val Gln His Lys Phe Val Glu Glu Ile
65                  70                  75                  80

Ile Glu Glu Thr Lys Val Glu Asp Glu Lys Ser Glu Met Glu Glu Ala
                85                  90                  95

Leu Thr Ala Ile Thr Glu Glu Leu Ala Val Ser Met Lys Glu Glu Lys
            100                 105                 110

Lys Glu Ala Ala Glu Glu Lys Glu Glu Glu Pro Glu Ala Glu Glu Glu
        115                 120                 125

Glu Val Ala Ala Lys Lys Ser Pro Val Lys Ala Thr Ala Pro Glu Val
    130                 135                 140

Lys Glu Glu Glu Gly Glu Lys Glu Glu Glu Gly Gln Glu Glu Glu
145                 150                 155                 160

Glu Glu Glu Asp Glu Gly Ala Lys Ser Asp Gln Ala Glu Glu Gly Gly
                165                 170                 175

Ser Glu Lys Glu Gly Ser Ser Glu Lys Glu Glu Gly Glu Gln Glu Glu
            180                 185                 190
```

-continued

```
Gly Glu Thr Glu Ala Glu Ala Glu Gly Glu Glu Ala Glu Ala Lys Glu
        195             200             205

Glu Lys Lys Val Glu Glu Lys Ser Glu Glu Val Ala Thr Lys Glu Glu
    210             215             220

Leu Val Ala Asp Ala Lys Val Glu Lys Pro Glu Lys Ala Lys Ser Pro
225             230             235             240

Val Pro Lys Ser Pro Val Glu Glu Lys Gly Lys Ser Pro Val Pro Lys
            245             250             255

Ser Pro Val Glu Glu Lys Gly Lys Ser Pro Val Pro Lys Ser Pro Val
            260             265             270

Glu Glu Lys Gly Lys Ser Pro Val Pro Lys Ser Pro Val Glu Glu Lys
    275             280             285

Gly Lys Ser Pro Val Ser Lys Ser Pro Val Glu Glu Lys Ala Lys Ser
    290             295             300

Pro Val Pro Lys Ser Pro Val Glu Glu Ala Lys Ser Lys Ala Glu Val
305             310             315             320

Gly Lys Gly Glu Gln Lys Glu Glu Glu Lys Glu Val Lys Glu Ala
            325             330             335

Pro Lys Glu Glu Lys Val Glu Lys Lys Glu Glu Lys Pro Lys Asp Val
        340             345             350

Pro Glu Lys Lys Lys Ala Glu Ser Pro Val Lys Glu Glu Ala Val Ala
        355             360             365

Glu Val Val Thr Ile Thr Lys Ser Val Lys Val His Leu Glu Lys Glu
    370             375             380

Thr Lys Glu Glu Gly Lys Pro Leu Gln Gln Glu Lys Glu Lys Glu Lys
385             390             395             400

Ala Gly Gly Glu Gly Gly Ser Glu Glu Glu Gly Ser Asp Lys Gly Ala
            405             410             415

Lys Gly Ser Arg Lys Glu Asp Ile Ala Val Asn Gly Glu Val Glu Gly
        420             425             430

Lys Glu Glu Val Glu Gln Glu Thr Lys Glu Lys Gly Ser Gly Arg Glu
        435             440             445

Glu Glu Lys Gly Val Val Thr Asn Gly Leu Asp Leu Ser Pro Ala Asp
    450             455             460

Glu Lys Lys Gly Gly Asp Lys Ser Glu Glu Lys Val Val Val Thr Lys
465             470             475             480

Thr Val Glu Lys Ile Thr Ser Glu Gly Gly Asp Gly Ala Thr Lys Tyr
            485             490             495

Ile Thr Lys Ser Val Thr Val Thr Gln Lys Val Glu Glu His Glu Glu
            500             505             510

Thr Phe Glu Glu Lys Leu Val Ser Thr Lys Lys Val Glu Lys Val Thr
        515             520             525

Ser His Ala Ile Val Lys Glu Val Thr Gln Ser Asp
    530             535             540

<210> SEQ ID NO 7
<211> LENGTH: 499
<212> TYPE: PRT
<213> ORGANISM: Homo sapiens

<400> SEQUENCE: 7

Met Ser Phe Gly Ser Glu His Tyr Leu Cys Ser Ser Ser Ser Tyr Arg
1               5               10              15
```

-continued

```
Lys Val Phe Gly Asp Gly Ser Arg Leu Ser Ala Arg Leu Ser Gly Ala
            20                  25                  30

Gly Gly Ala Gly Gly Phe Arg Ser Gln Ser Leu Ser Arg Ser Asn Val
            35                  40                  45

Ala Ser Ser Ala Ala Cys Ser Ser Ala Ser Ser Leu Gly Leu Gly Leu
    50                  55                  60

Ala Tyr Arg Arg Pro Pro Ala Ser Asp Gly Leu Asp Leu Ser Gln Ala
65                  70                  75                  80

Ala Ala Arg Thr Asn Glu Tyr Lys Ile Ile Arg Thr Asn Glu Lys Glu
                85                  90                  95

Gln Leu Gln Gly Leu Asn Asp Arg Phe Ala Val Phe Ile Glu Lys Val
            100                 105                 110

His Gln Leu Glu Thr Gln Asn Arg Ala Leu Glu Ala Glu Leu Ala Ala
            115                 120                 125

Leu Arg Gln Arg His Ala Glu Pro Ser Arg Val Gly Glu Leu Phe Gln
    130                 135                 140

Arg Glu Leu Arg Asp Leu Arg Ala Gln Leu Glu Glu Ala Ser Ser Ala
145                 150                 155                 160

Arg Ser Gln Ala Leu Leu Glu Arg Asp Gly Leu Ala Glu Glu Val Gln
                165                 170                 175

Arg Leu Arg Ala Arg Cys Glu Glu Glu Ser Arg Gly Arg Glu Gly Ala
            180                 185                 190

Glu Arg Ala Leu Lys Ala Gln Gln Arg Asp Val Asp Gly Ala Thr Leu
            195                 200                 205

Ala Arg Leu Asp Leu Glu Lys Lys Val Glu Ser Leu Leu Asp Glu Leu
    210                 215                 220

Ala Phe Val Arg Gln Val His Asp Glu Glu Val Ala Glu Leu Leu Ala
225                 230                 235                 240

Thr Leu Gln Ala Ser Ser Gln Ala Ala Ala Glu Val Asp Val Thr Val
                245                 250                 255

Ala Lys Pro Asp Leu Thr Ser Ala Leu Arg Glu Ile Arg Ala Gln Tyr
            260                 265                 270

Glu Ser Leu Ala Ala Lys Asn Leu Gln Ser Ala Glu Glu Trp Tyr Lys
            275                 280                 285

Ser Lys Phe Ala Asn Leu Asn Glu Gln Ala Ala Arg Ser Thr Glu Ala
    290                 295                 300

Ile Arg Ala Ser Arg Glu Glu Ile His Glu Tyr Arg Arg Gln Leu Gln
305                 310                 315                 320

Ala Arg Thr Ile Glu Ile Glu Gly Leu Arg Gly Ala Asn Glu Ser Leu
                325                 330                 335

Glu Arg Gln Ile Leu Glu Leu Glu Glu Arg His Ser Ala Glu Val Ala
            340                 345                 350

Gly Tyr Gln Asp Ser Ile Gly Gln Leu Glu Asn Asp Leu Arg Asn Thr
            355                 360                 365

Lys Ser Glu Met Ala Arg His Leu Arg Glu Tyr Gln Asp Leu Leu Asn
    370                 375                 380

Val Lys Met Ala Leu Asp Ile Glu Ile Ala Ala Tyr Arg Lys Leu Leu
385                 390                 395                 400

Glu Gly Glu Glu Thr Arg Phe Ser Thr Ser Gly Leu Ser Ile Ser Gly
                405                 410                 415

Leu Asn Pro Leu Pro Asn Pro Ser Tyr Leu Leu Pro Pro Arg Ile Leu
            420                 425                 430
```

```
Ser Ala Thr Thr Ser Lys Val Ser Ser Thr Gly Leu Ser Leu Lys Lys
        435                 440                 445

Glu Glu Glu Glu Glu Glu Ala Ser Lys Val Ala Ser Lys Lys Thr Ser
    450                 455                 460

Gln Ile Gly Glu Ser Phe Glu Glu Ile Leu Glu Glu Thr Val Ile Ser
465                 470                 475                 480

Thr Lys Lys Thr Glu Lys Ser Asn Ile Glu Glu Thr Thr Ile Ser Ser
                485                 490                 495

Gln Lys Ile

<210> SEQ ID NO 8
<211> LENGTH: 470
<212> TYPE: PRT
<213> ORGANISM: Homo sapiens

<400> SEQUENCE: 8

Met Ser His His Pro Ser Gly Leu Arg Ala Gly Phe Ser Ser Thr Ser
1               5                   10                  15

Tyr Arg Arg Thr Phe Gly Pro Pro Pro Ser Leu Ser Pro Gly Ala Phe
                20                  25                  30

Ser Tyr Ser Ser Ser Ser Arg Phe Ser Ser Ser Arg Leu Leu Gly Ser
            35                  40                  45

Ala Ser Pro Ser Ser Ser Val Arg Leu Gly Ser Phe Arg Ser Pro Arg
        50                  55                  60

Ala Gly Ala Gly Ala Leu Leu Arg Leu Pro Ser Glu Arg Leu Asp Phe
65                  70                  75                  80

Ser Met Ala Glu Ala Leu Asn Gln Glu Phe Leu Ala Thr Arg Ser Asn
                85                  90                  95

Glu Lys Gln Glu Leu Gln Glu Leu Asn Asp Arg Phe Ala Asn Phe Ile
                100                 105                 110

Glu Lys Val Arg Phe Leu Glu Gln Gln Asn Ala Ala Leu Arg Gly Glu
            115                 120                 125

Leu Ser Gln Ala Arg Gly Gln Glu Pro Ala Arg Ala Asp Gln Leu Cys
        130                 135                 140

Gln Gln Glu Leu Arg Glu Leu Arg Arg Glu Leu Glu Leu Leu Gly Arg
145                 150                 155                 160

Glu Arg Asp Arg Val Gln Val Glu Arg Asp Gly Leu Ala Glu Asp Leu
                165                 170                 175

Ala Ala Leu Lys Gln Arg Leu Glu Glu Glu Thr Arg Lys Arg Glu Asp
            180                 185                 190

Ala Glu His Asn Leu Val Leu Phe Arg Lys Asp Val Asp Asp Ala Thr
            195                 200                 205

Leu Ser Arg Leu Glu Leu Glu Arg Lys Ile Glu Ser Leu Met Asp Glu
        210                 215                 220

Ile Glu Phe Leu Lys Lys Leu His Glu Glu Glu Leu Arg Asp Leu Gln
225                 230                 235                 240

Val Ser Val Glu Ser Gln Gln Val Gln Gln Val Glu Val Glu Ala Thr
                245                 250                 255

Val Lys Pro Glu Leu Thr Ala Ala Leu Arg Asp Ile Arg Ala Gln Tyr
                260                 265                 270

Glu Ser Ile Ala Ala Lys Asn Leu Gln Glu Ala Glu Glu Trp Tyr Lys
            275                 280                 285

Ser Lys Tyr Ala Asp Leu Ser Asp Ala Ala Asn Arg Asn His Glu Ala
        290                 295                 300
```

-continued

```
Leu Arg Gln Ala Lys Gln Glu Met Asn Glu Ser Arg Arg Gln Ile Gln
305             310             315             320

Ser Leu Thr Cys Glu Val Asp Gly Leu Arg Gly Thr Asn Glu Ala Leu
            325             330             335

Leu Arg Gln Leu Arg Glu Leu Glu Glu Gln Phe Ala Leu Glu Ala Gly
        340             345             350

Gly Tyr Gln Ala Gly Ala Ala Arg Leu Glu Glu Glu Leu Arg Gln Leu
        355             360             365

Lys Glu Glu Met Ala Arg His Leu Arg Glu Tyr Gln Glu Leu Leu Asn
    370             375             380

Val Lys Met Ala Leu Asp Ile Glu Ile Ala Thr Tyr Arg Lys Leu Leu
385             390             395             400

Glu Gly Glu Glu Ser Arg Ile Ser Val Pro Val His Ser Phe Ala Ser
            405             410             415

Leu Asn Ile Lys Thr Thr Val Pro Glu Val Glu Pro Pro Gln Asp Ser
            420             425             430

His Ser Arg Lys Thr Val Leu Ile Lys Thr Ile Glu Thr Arg Asn Gly
        435             440             445

Glu Val Val Thr Glu Ser Gln Lys Glu Gln Arg Ser Glu Leu Asp Lys
    450             455             460

Ser Ser Ala His Ser Tyr
465             470
```